(12) United States Patent
Shvartsman et al.

(10) Patent No.: US 10,918,887 B2
(45) Date of Patent: Feb. 16, 2021

(54) METHOD AND APPARATUS FOR SHIELDING A LINEAR ACCELERATOR AND A MAGNETIC RESONANCE IMAGING DEVICE FROM EACH OTHER

(71) Applicant: ViewRay Technologies, Inc., Oakwood Village, OH (US)

(72) Inventors: Shmaryu M. Shvartsman, Highland Heights, OH (US); Gordon D. DeMeester, Wickliffe, OH (US); James F. Dempsey, Atherton, CA (US); John Lester Patrick, Chagrin Falls, OH (US)

(73) Assignee: VIEWRAY TECHNOLOGIES, INC., Oakwood Village, OH (US)

( * ) Notice: Subject to any disclaimer, the term of this patent is extended or adjusted under 35 U.S.C. 154(b) by 52 days.

(21) Appl. No.: 16/362,094

(22) Filed: Mar. 22, 2019

(65) Prior Publication Data

US 2019/0217126 A1    Jul. 18, 2019

Related U.S. Application Data

(63) Continuation of application No. 15/242,449, filed on Aug. 19, 2016, now Pat. No. 10,463,883, which is a
(Continued)

(51) Int. Cl.
*A61N 5/10*    (2006.01)
*G01R 33/38*    (2006.01)
(Continued)

(52) U.S. Cl.
CPC ............ *A61N 5/1049* (2013.01); *A61B 5/055* (2013.01); *A61B 5/0555* (2013.01);
(Continued)

(58) Field of Classification Search
CPC .............. A61N 5/1049; G01R 33/3806; G01R 33/421; G01R 33/4808; G01R 33/28; G01R 33/42; A61B 5/0555
See application file for complete search history.

(56) References Cited

U.S. PATENT DOCUMENTS

| | | | |
|---|---|---|---|
| 3,569,823 | A | 3/1971 | Golay |
| 3,735,306 | A | 5/1973 | Kabler |

(Continued)

FOREIGN PATENT DOCUMENTS

| | | |
|---|---|---|
| CN | 1394550 A | 2/2003 |
| CN | 1946339 | 4/2007 |

(Continued)

OTHER PUBLICATIONS

PCT App. No. PCT/US2010/042156; International Search Report and Written Opinion dated Sep. 10, 2010 ; 15 pages.
(Continued)

*Primary Examiner* — Dixomara Vargas
(74) *Attorney, Agent, or Firm* — Pillsbury Winthrop Shaw Pittman LLP

(57) ABSTRACT

A radiation therapy system comprises a magnetic resonance imaging (MRI) system combined with an irradiation system, which can include one or more linear accelerators (linacs) that can emit respective radiation beams suitable for radiation therapy. The MRI system includes a split magnet system, comprising first and second main magnets separated by gap. A gantry is positioned in the gap between the main MRI magnets and supports the linac(s) of the irradiation system. The gantry is rotatable independently of the MRI system and can angularly reposition the linac(s). Shielding can also be provided in the form of magnetic and/or RF shielding. Magnetic shielding can be provided for shielding the linac(s) from the magnetic field generated by the MRI
(Continued)

magnets. RF shielding can be provided for shielding the MRI system from RF radiation from the linac.

7 Claims, 16 Drawing Sheets

Related U.S. Application Data continuation of application No. 14/481,619, filed on Sep. 9, 2014, now Pat. No. 9,421,398, which is a continuation of application No. 12/837,309, filed on Jul. 15, 2010, now Pat. No. 8,836,332.

(60) Provisional application No. 61/225,771, filed on Jul. 15, 2009.

(51) Int. Cl.
   *G01R 33/421* (2006.01)
   *G01R 33/48* (2006.01)
   *A61B 5/055* (2006.01)
   *G01R 33/28* (2006.01)
   *G01R 33/42* (2006.01)

(52) U.S. Cl.
   CPC ......... *A61N 5/1039* (2013.01); *A61N 5/1081* (2013.01); *G01R 33/28* (2013.01); *G01R 33/3806* (2013.01); *G01R 33/42* (2013.01); *G01R 33/421* (2013.01); *G01R 33/4808* (2013.01); *A61N 2005/1055* (2013.01); *A61N 2005/1088* (2013.01); *A61N 2005/1089* (2013.01); *A61N 2005/1094* (2013.01)

(56) References Cited

U.S. PATENT DOCUMENTS

| | | | |
|---|---|---|---|
| 4,642,569 A | 2/1987 | Hayes | |
| 4,652,826 A | 3/1987 | Yamamoto | |
| 4,740,753 A | 4/1988 | Glover | |
| 5,006,804 A | 4/1991 | Dorri | |
| 5,280,428 A * | 1/1994 | Wu | G01R 33/56 250/363.04 |
| 5,295,488 A * | 3/1994 | Lloyd | G01R 33/56 324/309 |
| 5,331,552 A * | 7/1994 | Lloyd | G01R 33/56 378/15 |
| 5,361,763 A * | 11/1994 | Kao | G01R 33/56 382/145 |
| 5,365,927 A | 11/1994 | Roemer | |
| 5,373,239 A * | 12/1994 | Marek | G01R 33/3875 324/318 |
| 5,378,989 A | 1/1995 | Barber | |
| 5,530,352 A | 6/1996 | Kolem | |
| 5,585,724 A | 12/1996 | Morich | |
| 5,592,091 A | 1/1997 | Manabe | |
| 5,659,281 A | 8/1997 | Pissanetzky | |
| 5,675,305 A * | 10/1997 | DeMeester | G01R 33/3806 335/302 |
| 5,760,582 A | 6/1998 | Morrone | |
| 5,851,182 A | 12/1998 | Sahadevan | |
| 5,952,830 A | 9/1999 | Petropoulos | |
| 6,157,278 A * | 12/2000 | Katznelson | G01R 33/3806 324/319 |
| 6,198,957 B1 | 3/2001 | Green | |
| 6,311,389 B1 | 11/2001 | Uosaki | |
| 6,509,735 B2 | 1/2003 | Mueller | |
| 6,564,084 B2 | 5/2003 | Allred | |
| 6,591,127 B1 | 7/2003 | McKinnon | |
| 6,657,391 B2 | 12/2003 | Ding | |
| 6,788,060 B1 | 9/2004 | Feenan | |
| 6,806,712 B2 * | 10/2004 | Akgun | A61B 5/055 324/309 |
| 6,891,375 B2 | 5/2005 | Goto | |
| 6,940,281 B2 | 9/2005 | Feenan | |
| 7,012,385 B1 | 3/2006 | Kulish | |
| 7,162,005 B2 | 1/2007 | Bjorkholm | |
| 7,317,782 B2 | 1/2008 | Bjorkholm | |
| 7,394,081 B2 | 7/2008 | Okazaki | |
| 7,453,264 B2 * | 11/2008 | Trequattrini | G01R 33/383 324/318 |
| 7,489,131 B2 | 2/2009 | Lvovsky | |
| 7,535,229 B2 * | 5/2009 | Schlueter | G01R 33/381 324/307 |
| 7,728,311 B2 | 6/2010 | Gall | |
| 7,741,624 B1 | 6/2010 | Sahadevan | |
| 7,902,530 B1 | 3/2011 | Sahadevan | |
| 7,907,987 B2 * | 3/2011 | Dempsey | A61N 5/1064 600/411 |
| 7,957,507 B2 | 6/2011 | Cadman | |
| 8,139,714 B1 | 3/2012 | Sahadevan | |
| 8,173,983 B1 | 5/2012 | Sahadevan | |
| 8,190,233 B2 | 5/2012 | Dempsey | |
| 8,214,010 B2 | 7/2012 | Courtney | |
| 8,331,531 B2 | 12/2012 | Fahrig | |
| 8,334,697 B2 | 12/2012 | Overweg | |
| 8,378,677 B2 | 2/2013 | Morich | |
| 8,460,195 B2 | 6/2013 | Courtney | |
| 8,570,042 B2 * | 10/2013 | Pines | G01R 33/383 324/309 |
| 8,803,524 B2 | 8/2014 | Dempsey | |
| 8,836,332 B2 | 9/2014 | Shvartsman | |
| 8,896,308 B2 | 11/2014 | Shvartsman | |
| 8,981,779 B2 | 3/2015 | Shvartsman | |
| 8,983,573 B2 | 3/2015 | Carlone | |
| 9,114,253 B2 | 8/2015 | Dempsey | |
| 9,289,626 B2 | 3/2016 | Kawrakow | |
| 9,421,398 B2 | 8/2016 | Shvartsman | |
| 9,423,477 B2 | 8/2016 | Dempsey | |
| 9,446,263 B2 | 9/2016 | Dempsey | |
| 9,498,167 B2 * | 11/2016 | Mostafavi | A61N 5/1069 |
| 9,526,918 B2 | 12/2016 | Kruip | |
| 9,675,271 B2 | 6/2017 | Shvartsman | |
| 2003/0094947 A1 * | 5/2003 | Akgun | A61B 6/469 324/309 |
| 2003/0112107 A1 * | 6/2003 | Forbes | G01R 33/3875 335/301 |
| 2003/0197507 A1 | 10/2003 | Liu | |
| 2004/0239327 A1 | 12/2004 | Heid | |
| 2005/0030028 A1 | 2/2005 | Clarke | |
| 2005/0077899 A1 * | 4/2005 | Jacobs | H01F 1/0578 324/320 |
| 2005/0197564 A1 * | 9/2005 | Dempsey | G01R 33/381 600/411 |
| 2005/0197654 A1 | 9/2005 | Edman | |
| 2006/0033496 A1 | 2/2006 | Shvartsman | |
| 2006/0193441 A1 | 8/2006 | Cadman | |
| 2007/0003021 A1 | 1/2007 | Guertin | |
| 2007/0016014 A1 | 1/2007 | Hara | |
| 2007/0052420 A1 * | 3/2007 | Speck | G01R 33/3875 324/320 |
| 2007/0086569 A1 | 4/2007 | Johnsen | |
| 2008/0024130 A1 * | 1/2008 | Schlueter | G01R 33/383 324/309 |
| 2008/0049897 A1 | 2/2008 | Molloy | |
| 2008/0093567 A1 | 4/2008 | Gall | |
| 2008/0116894 A1 | 5/2008 | Weiger | |
| 2008/0177138 A1 | 7/2008 | Courtney | |
| 2008/0208036 A1 | 8/2008 | Amies | |
| 2008/0303457 A1 | 12/2008 | Maltz | |
| 2009/0060130 A1 | 3/2009 | Wilkens | |
| 2009/0147916 A1 * | 6/2009 | Fallone | A61N 5/1048 378/65 |
| 2009/0149735 A1 * | 6/2009 | Fallone | A61N 5/1049 600/411 |
| 2009/0264768 A1 | 10/2009 | Courtney | |
| 2010/0049030 A1 * | 2/2010 | Saunders | G01R 33/5673 600/411 |
| 2010/0113911 A1 | 5/2010 | Dempsey | |
| 2010/0239066 A1 * | 9/2010 | Fahrig | A61N 5/1049 378/65 |
| 2010/0322497 A1 | 12/2010 | Dempsey | |

(56) References Cited

U.S. PATENT DOCUMENTS

| | | | |
|---|---|---|---|
| 2011/0012593 A1* | 1/2011 | Shvartsman | G01R 33/28 324/307 |
| 2011/0118588 A1 | 5/2011 | Kornblau | |
| 2011/0121832 A1 | 5/2011 | Shvartsman | |
| 2011/0150180 A1 | 6/2011 | Balakin | |
| 2011/0218420 A1 | 9/2011 | Carlone | |
| 2011/0237859 A1 | 9/2011 | Kuhn | |
| 2011/0241684 A1 | 10/2011 | Dempsey | |
| 2011/0304416 A1* | 12/2011 | Warner | G01R 33/3815 335/216 |
| 2012/0019246 A1* | 1/2012 | Kannengiesser | G01R 33/5611 324/309 |
| 2012/0022363 A1 | 1/2012 | Dempsey | |
| 2012/0150017 A1 | 6/2012 | Yamaya | |
| 2012/0165652 A1 | 6/2012 | Dempsey | |
| 2012/0253172 A1 | 10/2012 | Loeffler | |
| 2013/0066135 A1 | 3/2013 | Rosa | |
| 2013/0090547 A1* | 4/2013 | Bani-Hashemi | A61N 5/1039 600/411 |
| 2013/0090549 A1 | 4/2013 | Meltsner | |
| 2013/0147476 A1* | 6/2013 | Shvartsman | G01R 33/3875 324/309 |
| 2013/0225975 A1* | 8/2013 | Harvey | A61B 5/0555 600/411 |
| 2013/0245425 A1 | 9/2013 | Dempsey | |
| 2013/0296687 A1 | 11/2013 | Dempsey | |
| 2013/0345556 A1 | 12/2013 | Courtney | |
| 2014/0003023 A1 | 1/2014 | Weibler | |
| 2014/0010355 A1 | 1/2014 | Seeber | |
| 2014/0084926 A1* | 3/2014 | Amthor | A61N 5/1049 324/309 |
| 2014/0121495 A1 | 5/2014 | Dempsey | |
| 2014/0135615 A1* | 5/2014 | Kruip | G01R 33/4808 600/411 |
| 2014/0263990 A1 | 9/2014 | Kawrykow | |
| 2014/0266206 A1 | 9/2014 | Dempsey | |
| 2014/0266208 A1 | 9/2014 | Dempsey | |
| 2014/0275963 A1 | 9/2014 | Shvartsman | |
| 2014/0330108 A1 | 11/2014 | Dempsey | |
| 2014/0336442 A1 | 11/2014 | Keppel | |
| 2014/0347053 A1 | 11/2014 | Dempsey | |
| 2015/0065860 A1* | 3/2015 | Shvartsman | G01R 33/42 600/411 |
| 2015/0077118 A1 | 3/2015 | Shvartsman | |
| 2015/0095044 A1 | 4/2015 | Hartman | |
| 2015/0154756 A1 | 6/2015 | Gerganov | |
| 2015/0165233 A1 | 6/2015 | Dempsey | |
| 2015/0185300 A1* | 7/2015 | Shvartsman | G01R 33/4814 324/322 |
| 2015/0251020 A1* | 9/2015 | Calone | A61B 5/055 600/1 |
| 2016/0011288 A1* | 1/2016 | Overweg | A61N 5/1039 600/411 |
| 2016/0067525 A1* | 3/2016 | Bouchet | A61N 5/1049 600/1 |
| 2016/0278719 A1* | 9/2016 | Jensen | A61B 6/4233 |
| 2016/0356869 A1 | 12/2016 | Dempsey | |
| 2017/0001039 A1 | 1/2017 | Dempsey | |
| 2017/0014644 A1* | 1/2017 | Shvartsman | G01R 33/3806 |
| 2017/0021198 A1 | 1/2017 | Kawrykow | |
| 2017/0120075 A1* | 5/2017 | Overweg | A61N 5/1081 |
| 2017/0176556 A1* | 6/2017 | Shvartsman | G01R 33/385 |
| 2017/0231583 A1 | 8/2017 | Goteti Venkata | |
| 2017/0252577 A1 | 9/2017 | Dempsey | |
| 2017/0371001 A1 | 12/2017 | Dempsey | |
| 2018/0003789 A1* | 1/2018 | Amthor | A61N 5/1049 |
| 2018/0021595 A1 | 1/2018 | Kesti-Helia | |
| 2018/0078785 A1 | 3/2018 | Ollila | |
| 2018/0078792 A1 | 3/2018 | Ollila | |
| 2018/0185669 A1 | 7/2018 | Kuusela | |
| 2018/0243584 A1 | 8/2018 | Nord | |
| 2019/0004131 A1* | 1/2019 | Wachowicz | A61N 5/1049 |
| 2019/0060670 A1* | 2/2019 | Ni | A61N 5/1049 |
| 2019/0083814 A1 | 3/2019 | Tallinen | |
| 2019/0090777 A1* | 3/2019 | Leghissa | A61B 5/055 |

FOREIGN PATENT DOCUMENTS

| | | |
|---|---|---|
| CN | 101309726 A | 11/2008 |
| CN | 101452065 A | 6/2009 |
| CN | 102247658 A | 11/2011 |
| CN | 102472830 A | 5/2012 |
| CN | 102713682 A | 10/2012 |
| EP | 0152554 A2 | 8/1985 |
| EP | 2230530 A1 | 9/2010 |
| EP | 2359905 A1 | 8/2011 |
| GB | 2393373 A | 3/2004 |
| JP | H03243877 A | 10/1991 |
| JP | H07148142 A | 6/1995 |
| JP | H07213507 A | 8/1995 |
| JP | 2001517132 A | 10/2001 |
| JP | 2004351207 A | 12/2004 |
| JP | 2005103295 A | 4/2005 |
| JP | 2007526036 A | 9/2007 |
| JP | 2008532681 A | 8/2008 |
| JP | 2009511222 A | 3/2009 |
| JP | 2009112870 A | 5/2009 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097864 A1 | 9/2006 |
| WO | 2007012933 A2 | 2/2007 |
| WO | 2007045076 A1 | 4/2007 |
| WO | 2008122899 A1 | 10/2008 |
| WO | 2009004521 A2 | 1/2009 |
| WO | 2009107005 A2 | 9/2009 |
| WO | 2009155700 A1 | 12/2009 |
| WO | 2010103644 A1 | 9/2010 |
| WO | 2011008969 A1 | 1/2011 |
| WO | 2011063342 A1 | 5/2011 |
| WO | 2012164527 A1 | 12/2012 |
| WO | 2015085008 A1 | 6/2015 |

OTHER PUBLICATIONS

EP App. No. 10800553.9; Extended EP Search Report dated Oct. 17, 2013; 10 pages.

EP App. No. 17000760.3; Extended EP Search Report dated Nov. 9, 2017.

Green et al. 'Split cylindrical gradient coil for combined PET-MR system.' Proc. Intl. Soc. Mag. Reson. Med. 16 (2008):352.

International Search Report issued by the European Patent Office in International Application No. PCT/US2014/023556 dated Jul. 18, 2014.

International Search Report of the International Searching Authority issued in International Application No. PCT/US2014/028792, dated Jul. 2, 2014.

Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.

Lagendijk JJ W et al.: "MRI Guided Radiotherapy: A MRI based linear Accelerator", Radiotherapy and Oncology, vol. 56, No. 01, Sep. 21, 2000 (Sep. 21, 2000), pp. S60-S61.

Lucas et al. 'Simultaneous PET-MR: toward a combined microPET. RTM.-MR system.' Proc. Intl. Soc. Mag. Reson. Med. 15(2007):922.

Overweg et al. 'System for MRI guided Radiotherapy.' Proc. Intl. Soc. Mag. Reson. Med. 17(2009):594.

Shvartsman et al. 'Gradient Coil Induced Eddy Current Computation Using the Boundary Elements Method.' Proc. Intl. Soc. Mag. Reson. Med. 17(2009):3055.

St. Aubin et al,, 'Magnetic decoupling on the linac in a low field biplanar linac-MR system', Med. Phys, 37 (9), Sep. 2010, pp. 4755-4761.

Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.

(56) References Cited

OTHER PUBLICATIONS

PCT App. No. PCT/US2017/020015; International Search Report and Written Opinion dated Jul. 26, 2017. 18 pages.
Office Action dated Nov. 15, 2018 for U.S. Appl. No. 15/242,449 (pp. 1-12).
CN App. No. 201610115787.5; Second Office Action dated Oct. 15, 2018.
AU App. No. 2017200361; Notice of Acceptance dated Oct. 30, 2018 (pp. 1-3).
Notice of Allownace dated Jun. 18, 2019 for U.S. Appl. No. 15/242,449 (pp. 1-11).
Office Action dated Jan. 24, 2018 for U.S. Appl. No. 15/620,800 (pp. 1-23).
Office Action dated Sep. 5, 2018 for U.S. Appl. No. 15/620,800 (pp. 1-19).
Office Action dated Oct. 22, 2018 for U.S. Appl. No. 15/268,366 (pp. 1-8).
Office Action dated Jan. 14, 2019 for U.S. Appl. No. 15/445,832 (pp. 1-11).
Office Action dated Apr. 17, 2019 for U.S. Appl. No. 15/268,366 (pp. 1-6).
Notice of Allowance dated Apr. 17, 2019 for U.S. Appl. No. 15/449,774 (pp. 1-5).
Notice of Allowance dated May 9, 2019 for U.S. Appl. No. 15/445,832 (pp. 1-5).
Notice of Allowance dated Jul. 1, 2019 for U.S. Appl. No. 15/268,366 (pp. 1-5).

\* cited by examiner

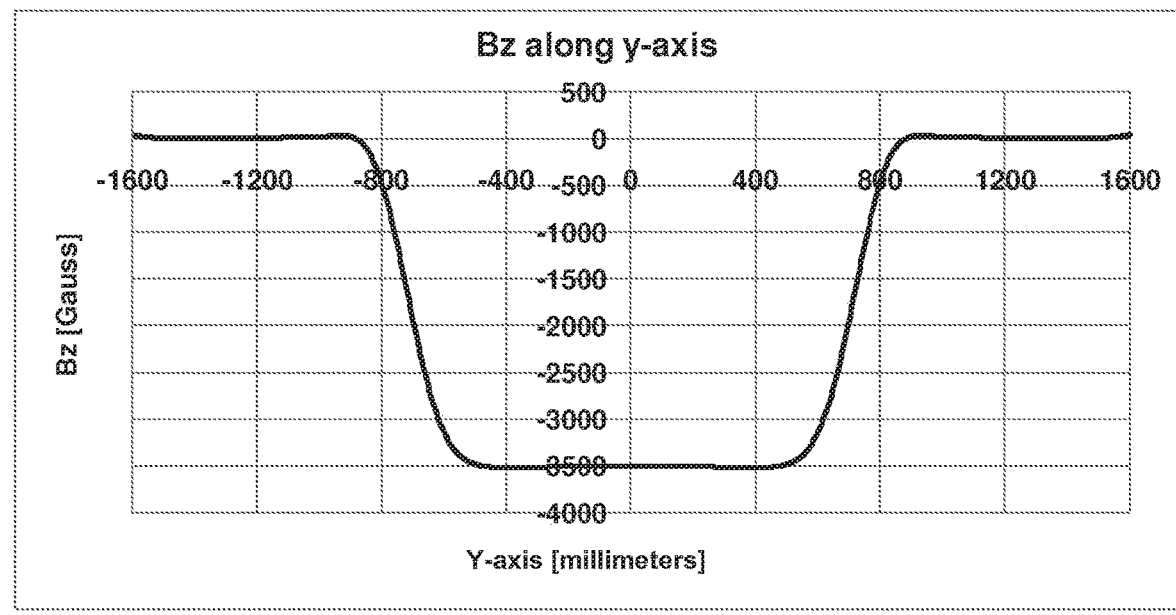
FIGURE 9
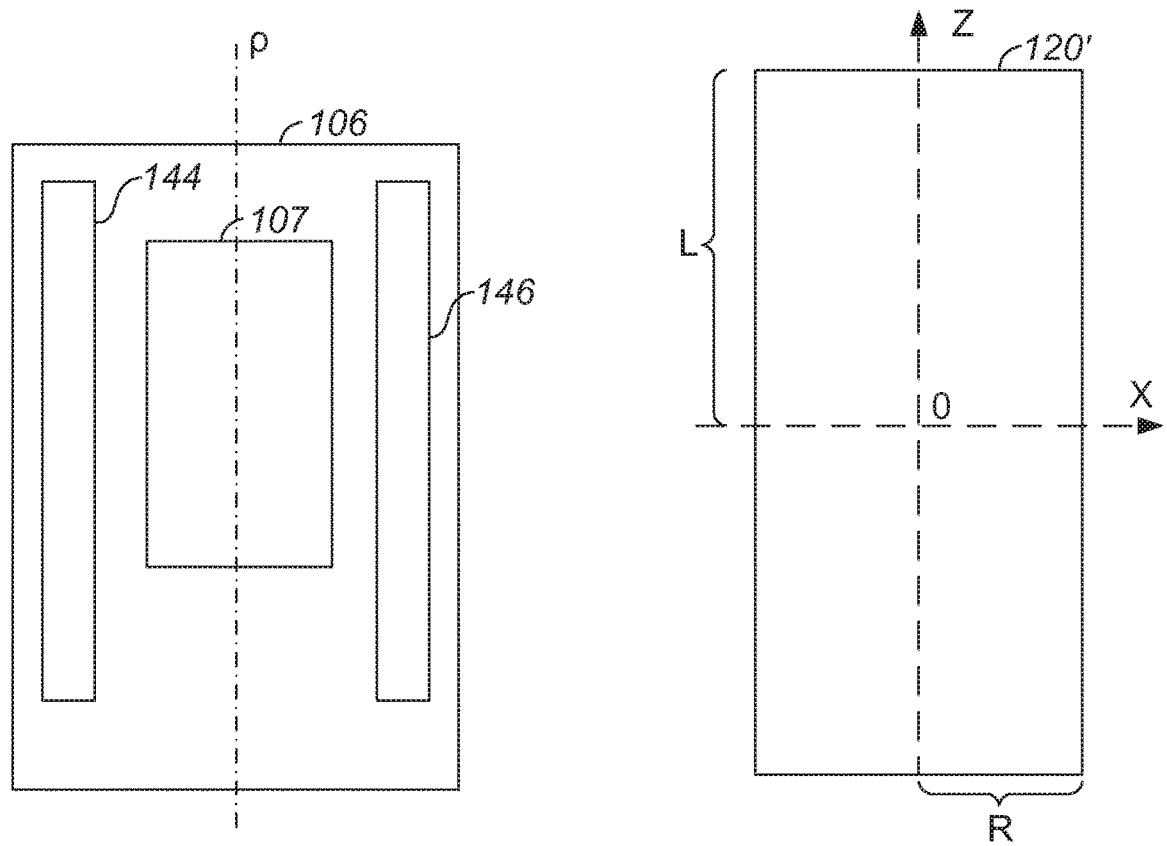
FIGURE 10
FIGURE 11

METHOD AND APPARATUS FOR SHIELDING A LINEAR ACCELERATOR AND A MAGNETIC RESONANCE IMAGING DEVICE FROM EACH OTHER

RELATED APPLICATION

This application is a continuation and claims benefit of priority under 35 U.S.C. § 120 of U.S. patent application Ser. No. 15/242,449, filed Aug. 19, 2016, entitled "Method And Apparatus For Shielding A Linear Accelerator And A Magnetic Resonance Imaging Device From Each Other," which claims the benefit of priority under 35 U.S.C. § 120 of U.S. patent application Ser. No. 14/481,619, filed Sep. 9, 2014 and issued as U.S. Pat. No. 9,421,398, entitled "Method And Apparatus For Shielding A Linear Accelerator And A Magnetic Resonance Imaging Device From Each Other", which claims the benefit of priority under 35 U.S.C. § 120 of U.S. patent application Ser. No. 12/837,309, filed Jul. 15, 2010 and issued as U.S. Pat. No. 8,836,332, entitled "Method And Apparatus For Shielding A Linear Accelerator And A Magnetic Resonance Imaging Device From Each Other", which claims the benefit of priority under 35 U.S.C. § 119 of U.S. Provisional Application No. 61/225,771, filed Jul. 15, 2009, entitled "Method And Apparatus For Shielding A Linear Accelerator And A Magnetic Resonance Imaging Device From Each Other". These references are incorporated herein by reference in their entirety for all purposes.

BACKGROUND

1. Technical Field

The present application relates to systems and methods for combined radiotherapy and magnetic resonance imaging, particularly systems and methods that involve shielding magnetic fields and radiofrequency radiation from the radiotherapy and magnetic resonance imaging systems.

2. Related Art

A linear particle accelerator (also called a linac) is a type of particle accelerator used to accelerate subatomic ions at great speeds. Linacs are described, for example, by C. J. KARZMARK ET AL., MEDICAL ELECTRON ACCELERATORS (McGraw-Hill, Inc., Health Professions Division 1993), which is hereby incorporated by reference. Medical grade or clinical linacs (a.k.a. clinacs) accelerate electrons using a tuned-cavity waveguide in which the Radio frequency (RF) power typically creates a standing or traveling wave for the generation of high energy electrons or Bremsstrahlung X-rays for medicinal purposes.

Magnetic Resonance Imaging (MRI), or nuclear magnetic resonance imaging (NMRI), is primarily a medical imaging technique most commonly used in radiology to visualize the internal structure and function of the body. MRI is described, for example, by E. MARK HAACKE ET AL., MAGNETIC RESONANCE IMAGING: PHYSICAL PRINCIPLES AND SEQUENCE DESIGN (Wiley-Liss 1999), which is hereby incorporated herein by reference.

It is desirable to be able to image with an MRI unit while being able to simultaneously perform radiation therapy using a linac. However, there are two major conflicts between the linac and MRI unit that should be overcome for these technologies to work together in a clinically acceptable way. The first problem is that the MRI unit's magnetic field accelerates charged particles in the linac by the Lorentz force on charged particles in a magnetic field determined by the equation $F=q(v \times B)$, where F is the force on the charged particle, q is the charge of the particle, v is the velocity, and B is the magnetic field. In linear accelerators, the electrons "ions" are typically generated by heating a thermionic material (a material where the electrons become detached when heated), which is the cathode, and when a positive voltage is applied to an anode (which is typically a wire grid), the electrons move from the cathode towards the anode. The anode is pulsed at 100's of megahertz such that the grouping of electrons pass thru the grid and on to be further accelerated. The cathode, anode, and later accelerating components form what is called the electron gun, and this gun can be shut down by an external magnetic field such that it will not produce electrons for further acceleration. The MRI magnet is usually shielded to reduce the magnetic field surrounding the magnet. Usually this magnetic fringe field remains above the level of the earth's 1 gauss magnetic field for a few meters from the MRI isocenter. The optimal distance for locating a linac near the patient is with the source at approximately one meter from the radiotherapy isocenter. For a system where the MRI and radiotherapy isocenters are substantially coincident, this puts the linac in a fringe field that could easily be on the order of 0.1 tesla (T, 1 T=10,000 gauss) or higher. The magnetic field B vector is significant and oriented axial to the MR system (Z). The velocity v vector approaches the speed of light and is nominally at right angles (Y) to the B vector. The force F on the very light electron will accelerate the electrons perpendicularly out of their desired trajectory.

The second problem is that the high-powered RF source of the linac causes interference with the radiofrequency transmitter and receiver for signal detection in the MRI unit. The RF frequency transmit and (especially) receive coils employed are extremely sensitive and usually limited by thermal noise in the patient and RF coil structure. Gradient magnetic fields are used to set a range of frequencies around this central frequency to provide position information as a function of frequency. The high-powered RF source in the linac typically generates megawatt to tens of megawatt bursts of RF radiation tuned to the resonating cavity of the accelerator at several hundred Hertz during operation. This high-powered RF radiation is typically not on resonance with the MRI frequencies of operation, but has side bands at the MRI frequencies and can induce eddy currents in the conducting components of the MRI causing signal corruption or even damaging the MRI electronics. MRI systems usually include an RF shielded room to limit interference from external RF sources. The sensitive MRI receive-RF coils also need to be protected from the RF transmit field used for excitation. Usually this isolation is done with PIN diodes and/or back-to-back diodes, switching in/out tuned/detuned circuit elements that attenuate the RF induced signal. Further, it is important that the sensitive MRI preamps do not go into saturation with RF energy from any source.

U.S. Pat. No. 6,198,957 to Green, titled "Radiotherapy Machine Including Magnetic Resonance Imaging System" (hereinafter "Green"), teaches the combination of a MRI system and a horizontal linac. Green teaches that DC coils should extend around the horizontal linac to shield the MRI from magnetic fields produced by the linac and that DC coils should be used around the MRI to shield the linac from the leakage magnetic field of the MRI. Also, Green teaches that, for a linac that uses an electron beam, the main magnets of the MRI must be pulsed off while the electron beam of the linac is pulsed on. In an analogous way, PCT International Publication WO2004/024235 to Lagendijk et al., titled "MRI in Guided Radiotherapy Apparatus with Beam Heterogeneity Compensators" (hereinafter "Lagendijk"), teaches integrating DC coils into the design of the main magnet of the MRI to create a toroidal low field region outside the MRI to shield the linac electron gun source from the MRI leakage magnetic field. Lagendijk also teaches the design of a main magnet that provides limited shielding on the electron gun of the linac and allows higher fields along the accelerating path toward the linac target, though this permits further degradation of the beam and that requires correction with additional filters. Again, in a similar way, PCT International Publication WO2007/045076 to Fallone et al., titled "Integrated External Beam Radiotherapy and MRI System" (hereinafter "Fallone"), teaches that a shielding interface between the MRI and linac can be used if the linac and MRI are fixed to each other to allow shimming, as was disclosed by Green. Also, Fallone teaches the use of steering coils associated with the linac for detecting and correcting for deviations of the linac electron beam due to the magnetic field of the MRI. Finally, U.S. Patent Application Publication 2008/0208036 to Amies et al., titled "Combined Radiation Therapy and Magnetic Resonance Unit" (hereinafter "Amies"), teaches that the linac can be placed completely inside the MRI main magnet bore with the path of the accelerated electrons aligned with the main magnetic field lines, however, this shortens the distance of the linac from isocenter. This also limits the beam path to be exactly along the central axis of the magnet. In a horizontal bore magnet, the magnetic field lines begin to diverge away from the central axis as you approach either end of the magnet, and in so doing turn in a radial direction. Thus, the beam must be exactly along the central axis or else it will be effected by the radial components of the field toward the ends. The MRI also uses "pulsed gradient fields" which can also have significant radial components off the central axis. Each of these references also teach the shielding of the linac from the MRI magnetic field where shielding material is interposed or interfacing between the beam source and the patient.

Prototypes of the devices taught by Lagendijk (and related its applications) and Fallone have demonstrated that the shielding leads to very large devices that cannot fit in the standard linac (or clinac) room and present many technical challenges where significant compromises must be made in the quality of the radiotherapy that can be delivered, either requiring the radiotherapy devices to treat from large distances or through a large amount of material that can scatter and attenuate the beam, compromising the quality of the radiotherapy. Additionally, these prototypes have employed RF shielding boxes that completely enclose the MRI from the linac and the treatment room, making patient access an issue.

As will be appreciated, there exists a need for an improved solution to the shielding of an MRI and linac from each other that, among other things, mitigates the disadvantages of having to pass the radiotherapy beams through a large amount of material or from long distances.

SUMMARY

Disclosed herein are methods and apparatus embodiments that allow for the production of a combined linac and MRI device. A method of shielding the RF radiation of the linac without sealing off the MRI is also described. Embodiments disclosed herein describe shielding to isolate the linac from the magnetic field of the MRI magnet and the RF transmit/receive coils from the linac RF field. A novel method of shielding the linac from the leakage magnetic field of the MRI at the standard position, i.e., about one meter from the radiotherapy isocenter, without placing shielding material between the patient and the incident beam, thereby preventing the degradation of the beam, is taught with shimming and correction of the homogeneous MRI magnetic field with gantry and MRI bore mounted shims; the gantry mounted shims being able to rotate with the linac. Magnetic shielding can be done with ferromagnetic shields and local coils, or combinations thereof, that are placed around the linac, yet not in the path of the beam. RF shielding of the MRI system is achieved by the selective use of a combination of uniform RF radiation absorbing materials, such as carbon fiber mesh, and RF radiation reflective materials, such as copper shielding. The beam is allowed to pass through the RF shielding as it can be constructed to be part of the flattening filter attenuation or can be made with a thin section or hole to pass the beam. The absorbing and attenuating materials can be layered successively to reflect, attenuate, and/or absorb the RF radiation from the linac. Cooling can be provided to the absorbing material as necessary to remove heat generated by the RF radiation being absorbed.

According to some aspects of the present disclosure, a magnetic shield can be provided about a linac. The shield can include one or more shells of high magnetic susceptibility and permeability layers, current carrying coils, permanent magnets, or any combination thereof, to shield the linac from the magnetic field of a MRI system in order to allow for proper operation of the linac. The shells are preferably cylindrical, but other shapes can be used.

In embodiments that include more than one of the shells, the shells are preferably magnetically isolated from each other.

The shield can be arranged so that the magnetic field of the MRI system does not attenuate the radiotherapy beam. The shield can operate at a preferred distance for linac placement. The inner layers of the shield can have higher permeability but saturate at a lower flux density. The influence of the shield on the homogeneous region of the MRI magnetic field can be diminished and balanced by an opposed dummy shield.

The influence of the shield on the MRI magnetic field can be corrected by shims. For example, gantry mounted shims can correct perturbations that follow the gantry angle of linac. MRI bore mounted shims and/or magnet design can correct for perturbations that are independent of the gantry angle of the linac.

According to further aspects of the present disclosure, an RF shield about a linac can include one or more layers of RF absorbing materials, and/or RF reflecting materials, or combinations of both, to contain the RF radiation and/or shield the MRI from the high power RF radiation produced by the linac in order to allow for proper operation of the MRI.

The RF shield can be arranged so that the beam passes through the shield with uniform attenuation. The RF shield can also be arranged so that the flattening filter is part of the RF shield. A thin section or hole can be used to limit beam attenuation.

Shielding can be improved by the application of RF absorbing materials to one or more of the RF room interior walls, the MRI surfaces, and the former for winding the gradient coils.

BRIEF DESCRIPTION OF THE DRAWINGS

Features, aspects, and embodiments of the inventions are described in conjunction with the attached drawings, in which:

FIG. 9 shows the Bz-field generated by the main MRI magnets as shielded according to some embodiments;

FIG. 10 shows a simplified block diagram of some embodiments of the system shown in FIGS. 1A-1D;

FIG. 11 shows an embodiment of an active shield that can be used in some embodiments of the system shown in FIGS. 1A-1D.

DETAILED DESCRIPTION

Figure 1A:
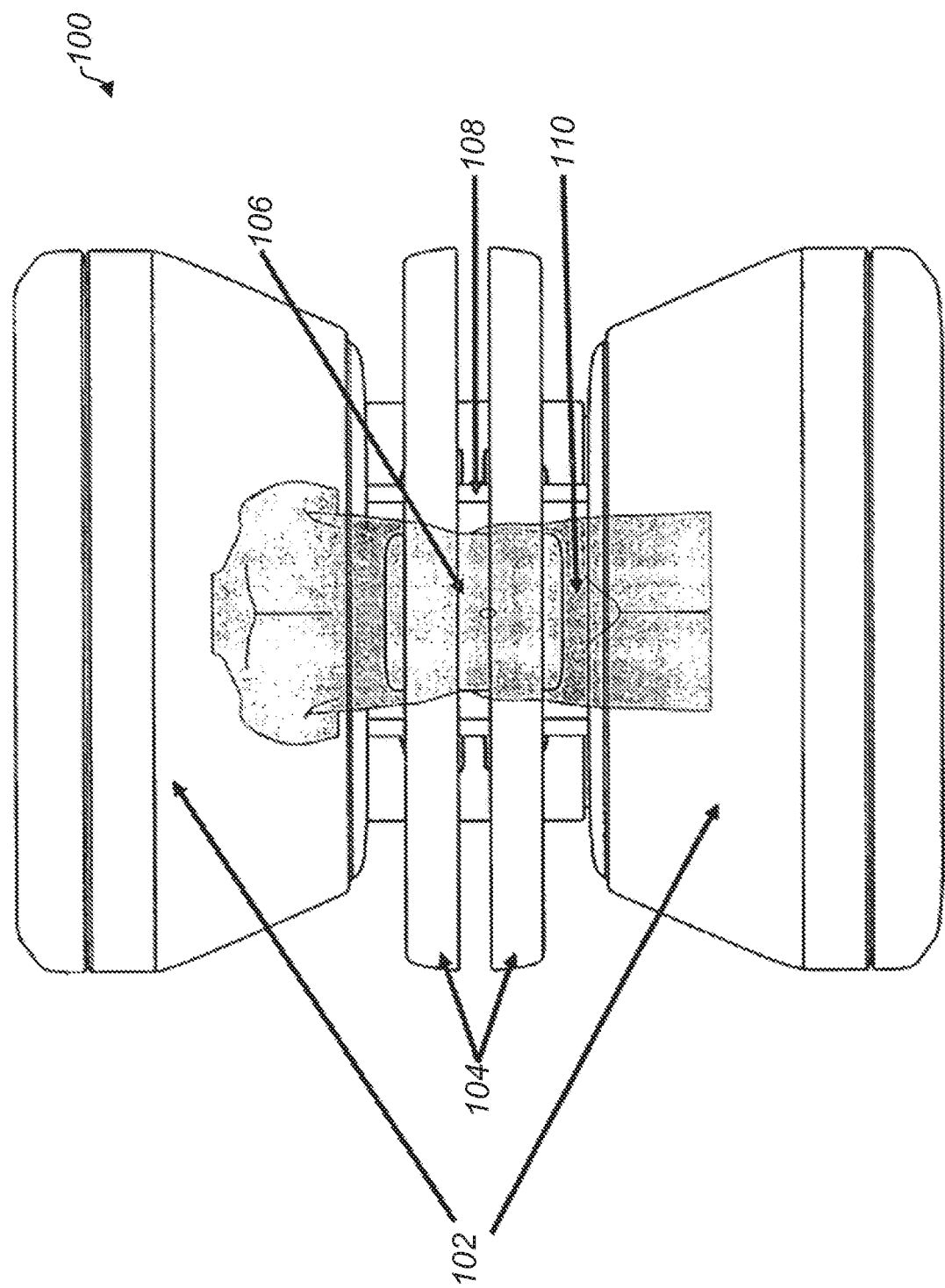
FIG. 1A shows a plan view of a split-magnet radiation therapy system.
Figure 1B:
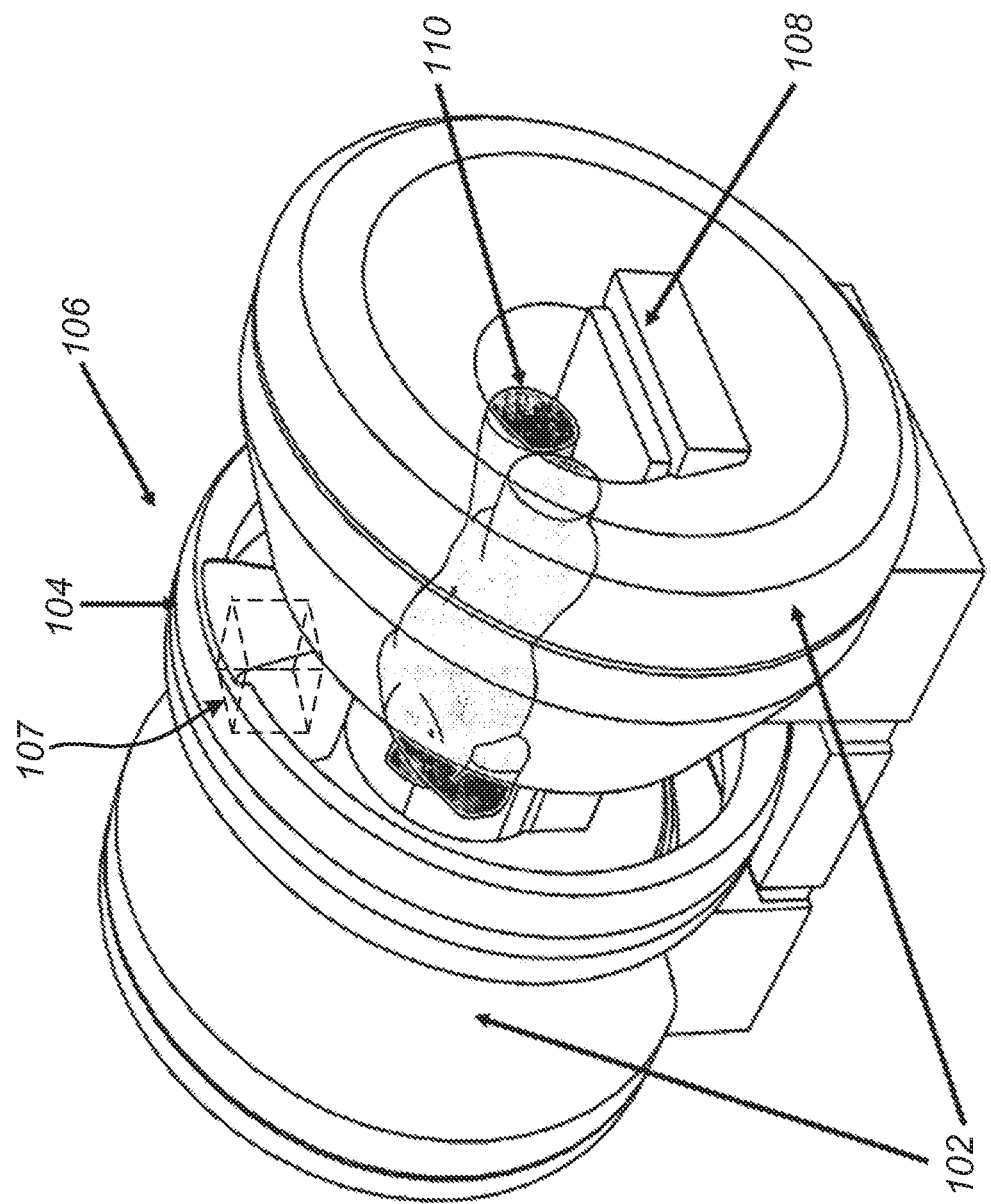
FIG. 1B shows a perspective view of the split-magnet radiation therapy system shown in FIG. 1A.

FIGS. 1A-1E show various views of a split-magnet radiation therapy system 100. FIGS. 1A and 1B show plan and perspective views, respectively, of a split-magnet radiation therapy system 100. The system 100 includes an integrated linear accelerator 107 and MRI system 102, and allows for simultaneous irradiation from the linear accelerator 107 and imaging from the MRI 102. For example, the MRI 102 can be used to pinpoint the location of an object to be irradiated, and this information can be used to control the irradiation from the linear accelerator 107. The present disclosure is not necessarily limited to the specific MRI and linac systems shown in the Figures and referenced herein, but can apply equally to other MRI and linac systems. For example, RF and/or magnetic shielding systems and methods disclosed herein can be used with known MRI and linac systems that may differ from those shown in the Figures and described below.

The radiation therapy system 100 includes an open split solenoidal magnetic resonance imaging (MRI) device 102, a radiation source 104, a gantry 106 for housing a linac 107 and for changing the angle of radiation source 104, a patient couch 108, and a patient 110 in position for imaging and treatment. A similar system is described in U.S. Patent Application Publication 2005/0197564 to Dempsey, titled "System for Delivering Conformal Radiation Therapy while Simultaneously Imaging Soft Tissue" (hereinafter "Dempsey '564"), which is hereby incorporated by reference.

The radiation therapy system 100 of the present disclosure differs in many respects from that disclosed in Dempsey '564, a primary difference being that the radiation therapy system 100 of the present disclosure includes a linac 107 rather than the isotopic radiation system disclosed in Dempsey '564. Except as described herein, the linac 107 can be of conventional design. In some embodiments, the linac 107, best shown in FIG. 1E, can be a medical grade or clinical linac (clinac) configured to accelerate electrons using a tuned-cavity waveguide 107a in which the Radio frequency (RF) power creates a standing or traveling wave for the generation of high energy electrons from an electron gun 107b. An optional target 107c can be included that is installed for x-ray/photon-beam therapy and removed for electron-beam therapy. The X-ray/photon beams and electron beams constitute examples of linac radiation beams. In some embodiments, the system 100 can include a pre-collimator 107d and a multi-leaf collimator 107e, for example as disclosed in Dempsey '564, for the electron beam EB from the linac 107. As discussed in greater detail below, the linac 107, particularly the waveguide 107a, can be protected by magnetic and/or RF shielding 118, 120, and/or 122. The magnetic and/or RF shielding 118, 120, and/or 122 can be in the form of one or more shells that are preferably cylindrical, but other shapes can be used. Also, as discussed in greater detail below, the radiation therapy system 100 can include a cooling system 115 for cooling the shielding 118, 120, and/or 122. The cooling system 115 can include, for example, liquid and/or air cooling systems.

Figure 1C:
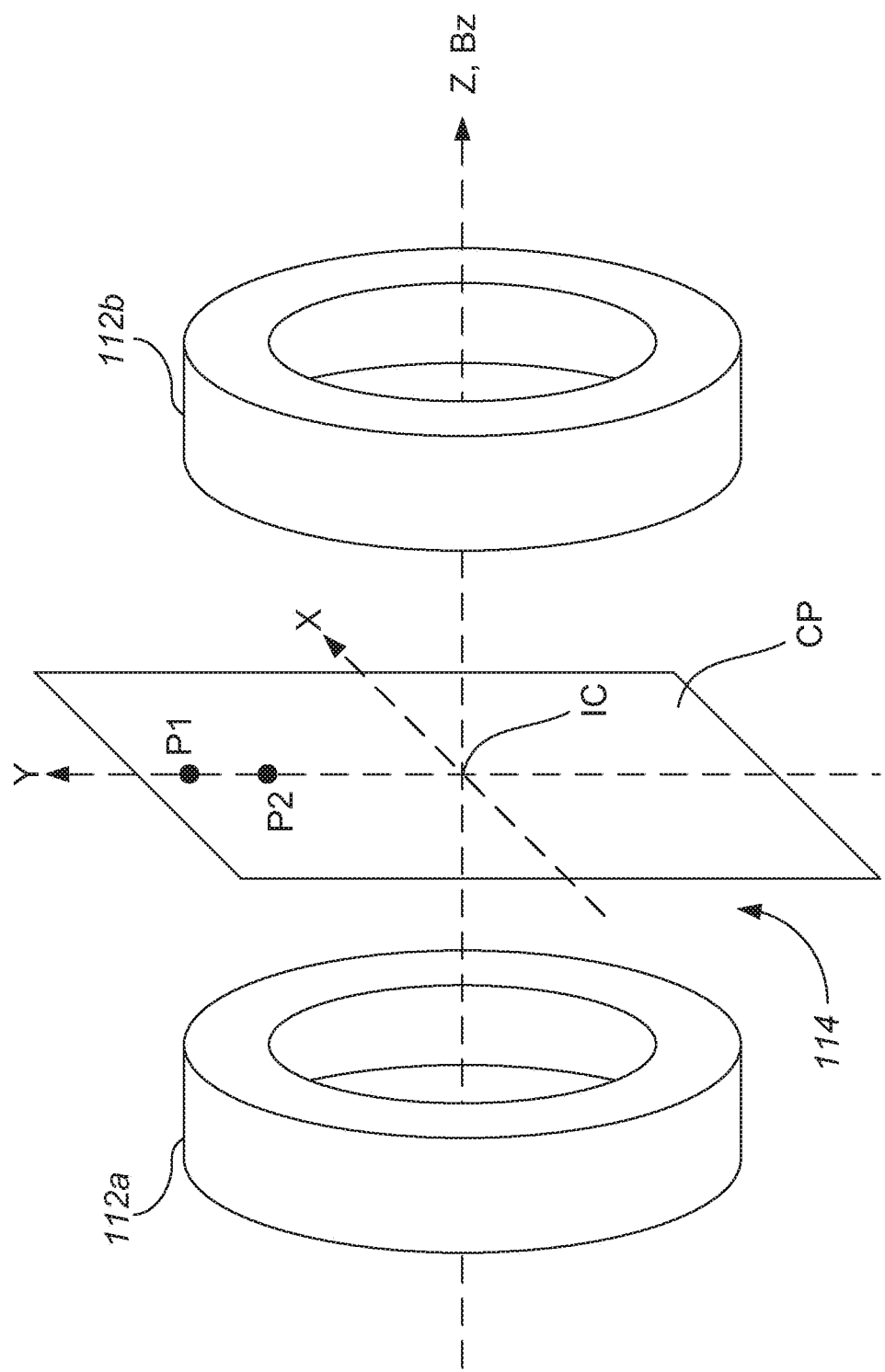
FIG. 1C shows a simplified block diagram of the split-magnet radiation therapy system shown in FIG. 1A.

The radiation therapy system 100 can include a split magnet system, such as described in Dempsey '564. The split magnet system includes a pair of main magnets 112a and 112b as shown in FIG. 1C as part of the MRI device 102. The MRI device 102 can also include conventional MRI components that are not shown, such as a split gradient coil, one or more shim coils (also referred to as shims), and an RF system, including RF coils. The strength of the magnetic field generated by the main magnets 112a and 112b can vary. However, for convenience of explanation, the system 100 will be described with reference to an embodiment where the main magnet field strength is 0.35 T, which is chosen to prevent perturbations in the dose distribution caused by the Lorentz force acting on secondary electrons in the patient. The magnets 112a and 112b are separated by a central gap 114, for example of 0.28 m. The MRI device 102 can be designed to provide an MRI field-of-view of, for example, 50 cm diameter around a center of the image field, and at the same time provide an un-attenuated radiation beam in the gap 114 with the split gradient coil of the MRI device 102. Preferably, the system 100 is constructed such that the radiation beam from the split gradient coil only passes through RF coils, the patient 110, and the patient couch 108.

Figure 1D:
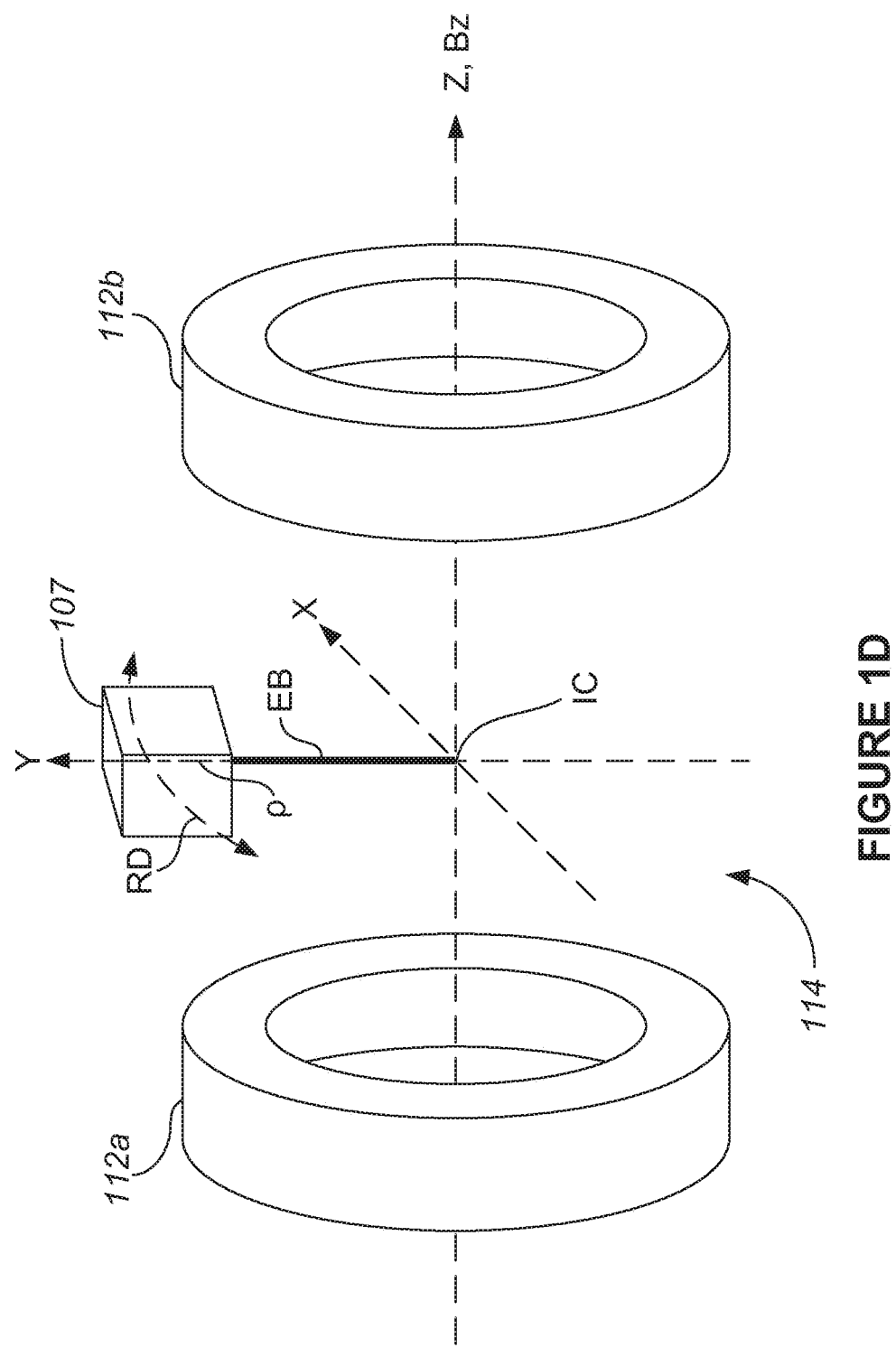
FIG. 1D shows another simplified block diagram of the split-magnet radiation therapy system shown in FIG. 1A.
Figure 1E:
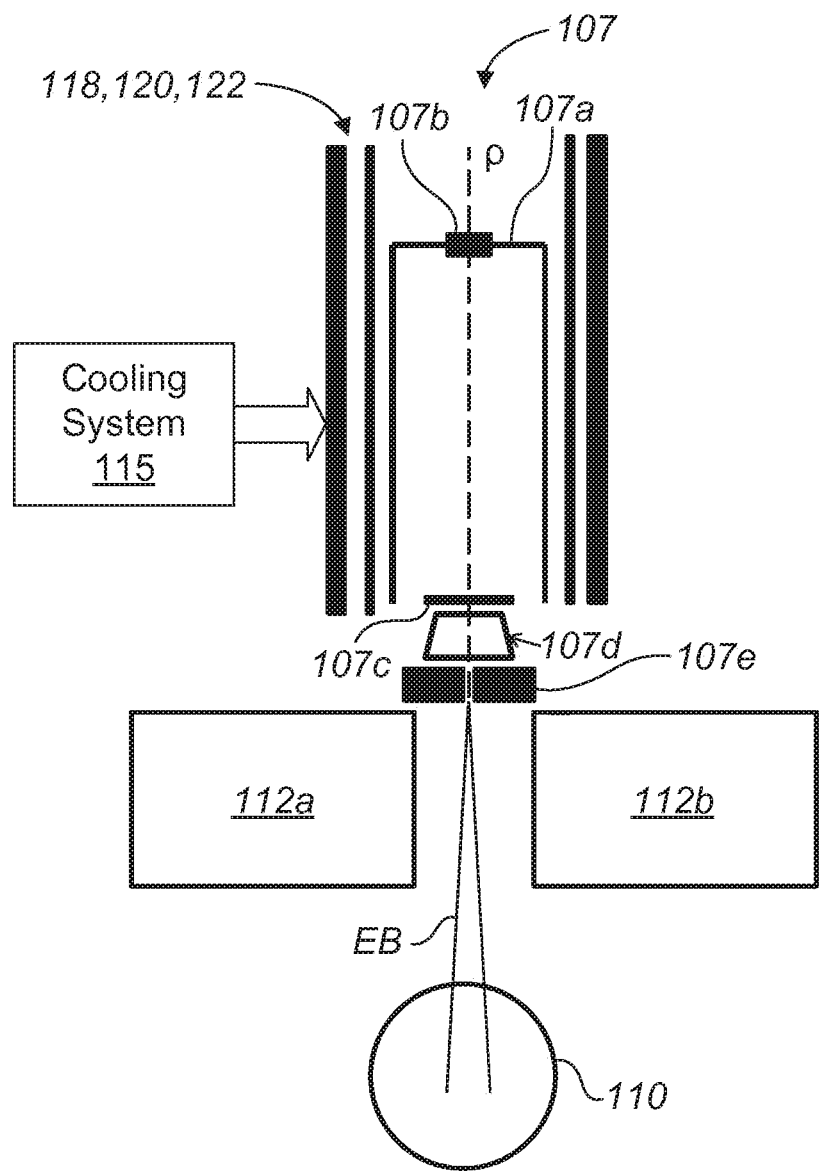
FIG. 1E shows another simplified block diagram of the split-magnet radiation therapy system shown in FIG. 1A.

FIGS. 1C and 1D show a simplified block diagrams of the system 100. In FIG. 1C, only the main magnets 112a and 112b of the MRI system 102 are illustrated; in FIG. 1D only the main magnets 112a and 112b and the linac 107 are illustrated. The coordinate system shown in FIGS. 1C and 1D, and used throughout this disclosure, refers to the longitudinal axis through the MRI bore (lengthwise through patient 110) as the Z-axis. The Z-axis is normal to a central axial plane CP, also referred to as transverse or central plane CP, which is at least substantially centered within the gap 114 between the main magnets 112a and 112b. Also, the main magnets 112a and 112b both extend radially about the Z-axis. The central plane CP is also defined by an X-axis and a Y-axis. The X-axis extends perpendicular to the Z-axis and from side to side of the MRI system 102; the Y-axis extends perpendicular to the Z-axis and from bottom to top of the MRI system 102.

In the system 100 of the present embodiment, at a distance of 1 m from magnet isocenter IC on the central plane CP, there is a magnetic field of Bz z 0.1 T, shown as point P1, which is a desired distance from isocenter for the source of the radiation of the linac 107. The magnetic field reverses direction from +Bz to −Bz at a radial distance of 0.81 m, shown as point P2. The magnet field at 1 m from isocenter, where the linac 107 radiation source is preferrably located for optimal radiotherapy operation, is low enough that it can be contained in a ferromagnetic shield or multiple layered shields, as described below. In the central axial plane CP, there is mainly axial magnetic field Bz because of coil symmetry. In the central plane CP, we assume that Y is a vertical axis and the axis of a high magnetic susceptibility (and/or permeability in a linear domain) material, e.g., a non-oriented silicon-steel shell, for shielding the linac 107.

Figure 2A:
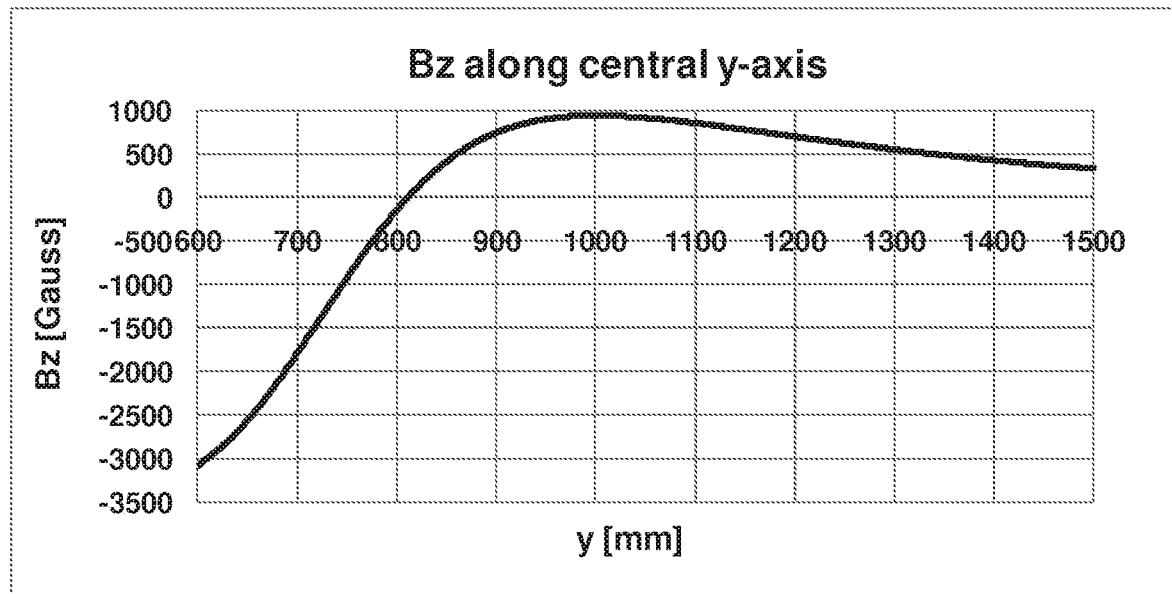
FIGS. 2A and 2B shows charts of a magnetic field generated by main magnets of an MRI of the system shown in FIGS. 1A-1D.
Figure 2B:
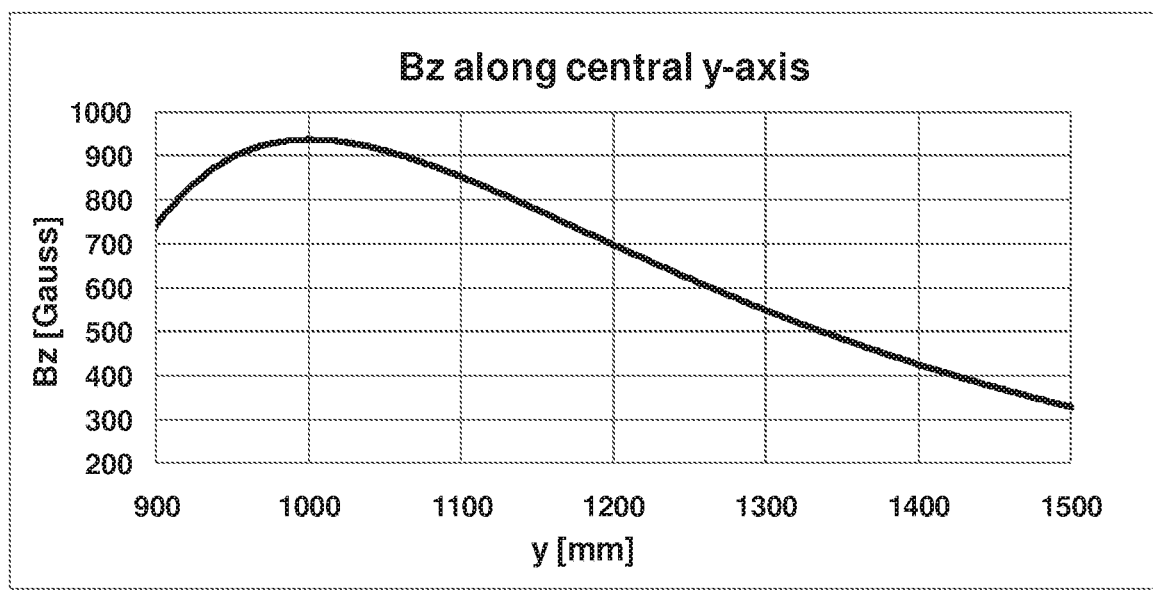

The field generated by the main magnets 112a and 112b near the central plane CP is shown in FIG. 2A. For the linac 107 to operate properly, it is desirable for the magnetic field in the center of the accelerating structure to be much less than the unshielded magnetic field near Y=1000 mm (e.g., point P1). FIG. 2A also shows that there is a null point (Bz=0) in the vicinity of y≈810 mm where the Bz field reverses direction, as must always happen due to the reversal of field direction. FIG. 2B shows the same field in the region of interest near Y=900 mm, but with a rescaled Y-axis.

The linac 107 has a longitudinal axis p that is aligned with the Y-axis in FIG. 1D. While the linac 107 is shown and described as being aligned along the Y-axis, it is preferable for the linac 107 to be rotatable about the Z-axis. For example, the gantry 106 shown in FIGS. 1A and 1B can support the linac 107 and carry the linac 107 about the Z-axis (while the longitudinal axis p remains in the central plane CP), in the rotation directions RD shown in FIG. 1D, such that the linac 107 can emit an electron beam EB towards the isocenter IC from any, or a range of, rotational positions about the Z-axis. Also, the gantry 106 and linac 107 can rotate about the Z-axis independently of other components of the system 100. For example, the gantry 106 and linac 107 can rotate independently of the MRI 102.

Figure 3A:
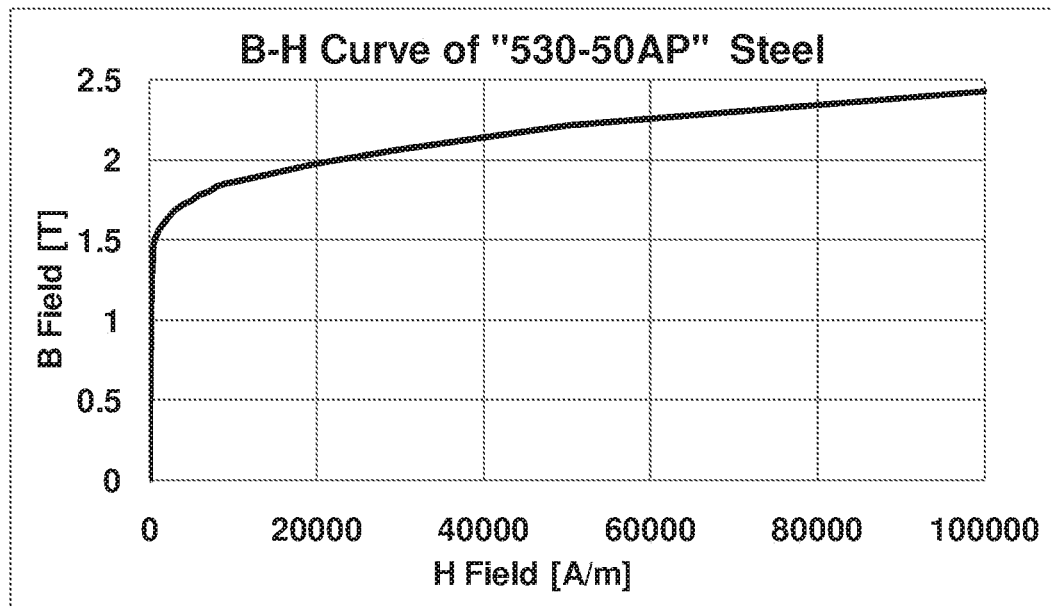
FIGS. 3A and 3B show charts of the B-H curve and the relative permeability, respectively, of magnetic shielding material used in some embodiments of the system shown in FIGS. 1A-1D.
Figure 3B:
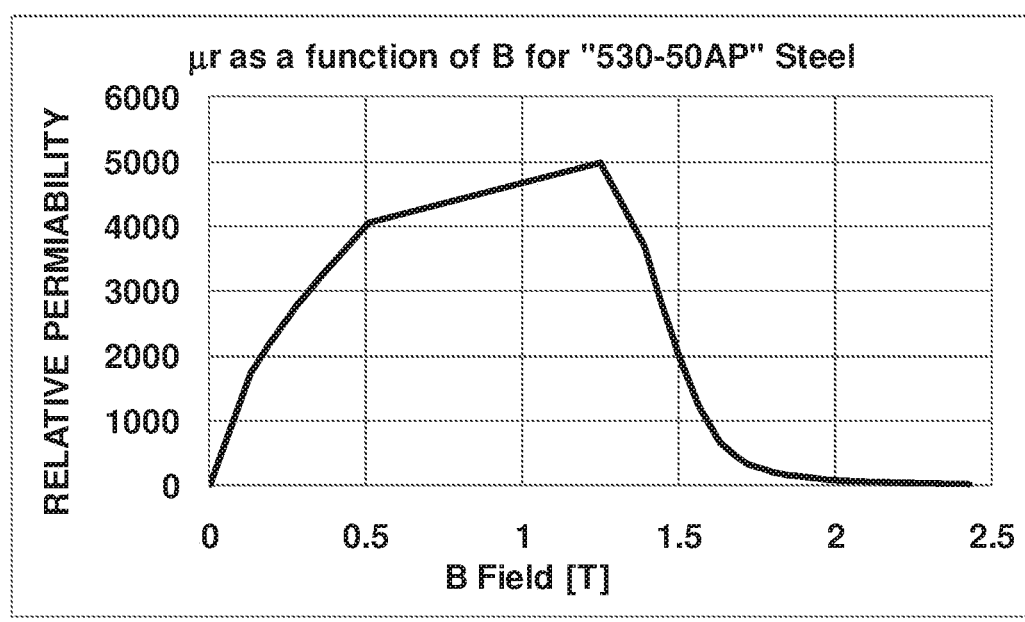

Turning next to FIGS. 3A-3B and FIGS. 4A-4B, we now describe a general method for magnetically shielding the linac 107 from the magnetic field of the MRI system 102. Although specific examples are provided, this does not exclude similar approaches or variations in form or material to achieve the same goal. To suppress the magnetic field B in the region where the linac 107 is located, a magnetic shield or shell 118 made of high magnetic susceptibility and permeability material, is placed around the linac accelerating structure 107. The shell 118 can be cylindrical in shape and aligned along axis p of the linac 107, with one or both ends of the shell 118 being open. While a cylindrical shape is preferred, the disclosed shield shells can be other shapes. At least one end of the shell 118 is open for the electron beam EB (shown in FIG. 1D) from the linac 107. The magnetic shield 118 can have a thickness chosen according to characteristics of the shell material. The magnetic shield 118 (as well as other magnetic shields disclosed herein) can be formed of non-oriented silicon steel, for example a nickel-iron alloy, such as commercially-available material sold by ThyssenKrupp Steel under the trade name 530-50 AP and having a thickness of, for example, about be 5 mm. The B-H curve and relative permeability of "530-50AP" material are shown in FIGS. 3A and 3B, respectively. Other material options for the magnetic shield 118 (as well as other magnetic shields disclosed herein) include M19 steel, M45 steel, and Carpenter High Permeability "49" Steel.

Figure 4A:
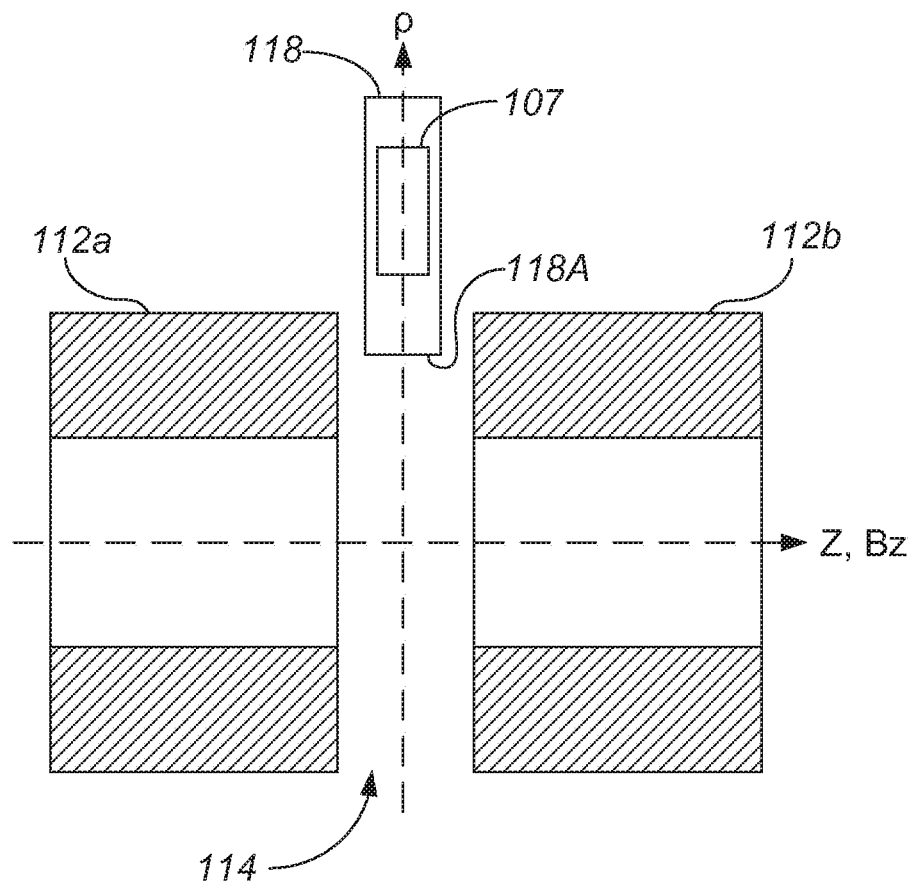
FIG. 4A shows a simplified block diagram of some embodiments of the system shown in FIGS. 1A-1D, including a section view of the main magnets shown in FIGS. 1C and 1D.
Figure 4B:
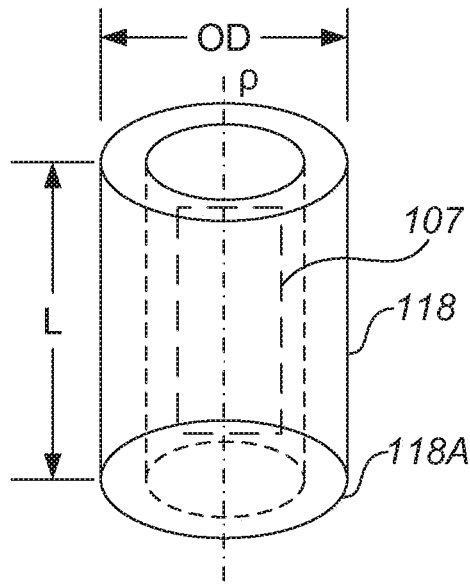
FIGS. 4B-4E show more detailed views of embodiments of the shielding that can be used with the system shown in FIGS. 1A-1D.
Figure 4C:
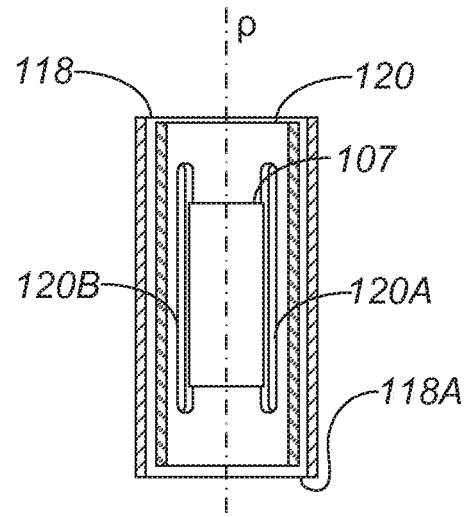

The magnets 112a and 112b, and the location of the magnetic shield 118, are illustrated in FIG. 4A, while a close-up perspective view of the magnetic shield 118 and linac 107 are shown in FIG. 4B. The outer diameter OD and length L of the magnetic shield 118 can vary; in the present embodiment, the outer diameter OD is about 30 cm, and the length L is about 70 cm. A bottom edge 118A of the magnetic shield 118 is located at a fixed distance from the isocenter IC (in the present embodiment, about 80 cm) that is at or near the Bz field reversal location, although this is not a requirement. The location and size of the magnetic shield 118 should be large enough to contain the linac 107, but not so long or narrow that it limits the size of the beam emitted by the linac 107. The magnetic shield 118 configuration is optimal for radiotherapy applications when combined with split main magnets 112a and 112b and gradient coil set, as the magnetic shield 118 is not imposed between the radiation source of the linac 107 and the patient 110. This allows for producing radiotherapy beams of the linac 107 of high quality and strength. In some embodiments, such as shown in FIG. 4C, the magnetic shielding can be provided by multiple shield shells. In FIG. 4C, the magnetic shielding is provided by the magnetic shield 118 and a second magnetic shield 120, where the shields 118 and 120 can be concentric layers of steel, which can be separated by layers of air or other insulating material.

Figure 5A:
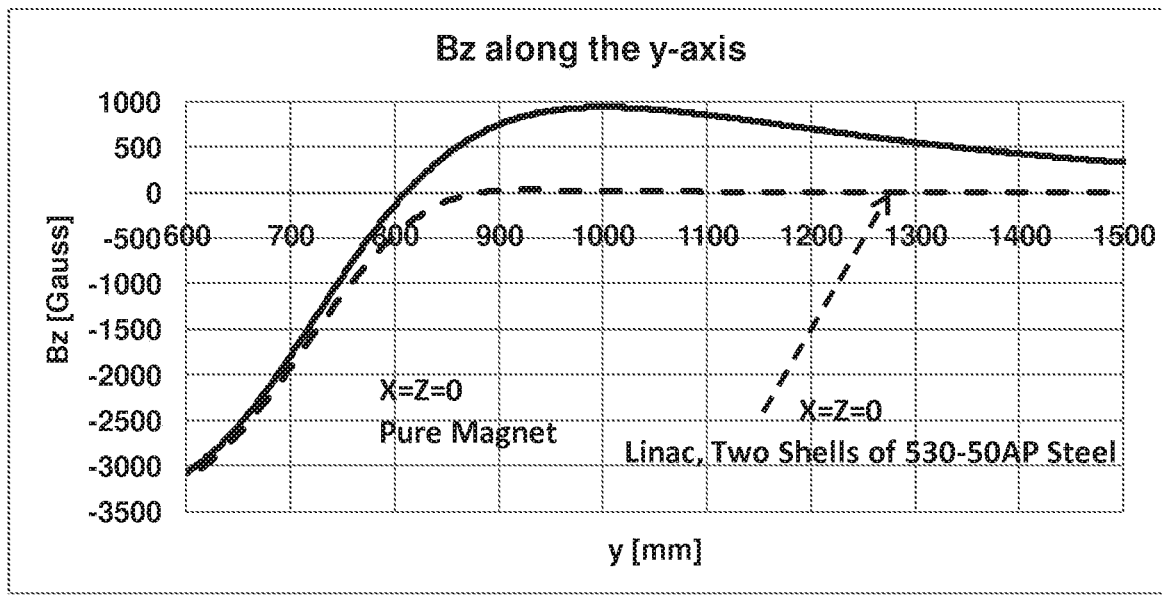
FIGS. 5A and 5B show a comparison of the shielded and unshielded Bz-field generated by the main magnets of the MRI according to some embodiments.
Figure 5B:
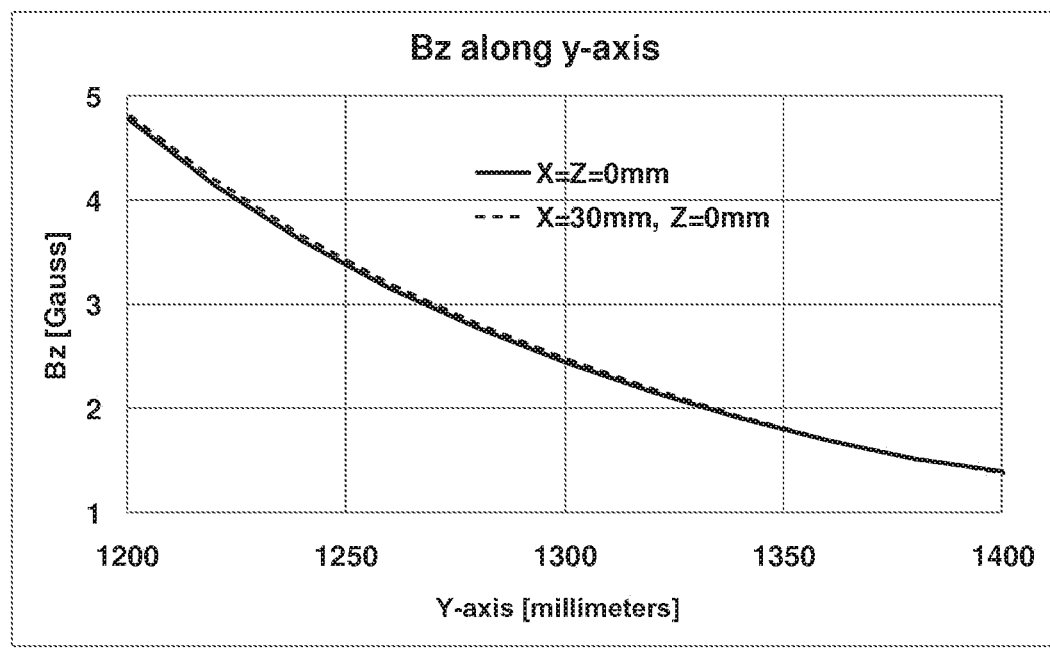

The model of the influence of the material, which in this embodiment is steel, in the presence of the main magnets 112a and 112b was solved using Maxwell's equations via the boundary element method. FIG. 5A shows a comparison of the Bz-field generated by the main magnets 112a and 112b, and the z-component of the Bz-field generated by the main magnets 112a and 112b as shielded by an embodiment where the magnetic shielding comprises an outer magnetic shield 118 and an inner magnetic shield 120, where the shields 118 and 120 are separated by a layer of air. FIG. 5B shows a close-up view of FIG. 5A of the region of interest near Y=1200 mm of the z-component of the Bz-field generated by the main magnets 112a and 112b as shielded by the magnetic shields 118 and 120. Table 1 lists the materials and dimensions of the magnetic shields 118 and 120 according to the embodiment associated with FIGS. 5A and 5B. In Table 1, "ID" is the inner diameter, "OD" is the outer diameter, Length is the shell length L, and the "Starting Y-position" is the distance from the isocenter (Z-axis) to the respective bottom edges of the shields 118 and 120.

TABLE 1

Two Shells of 530-50AP Steel

| Layer | ID [mm] | OD [mm] | Length [mm] | Starting Y-position [mm] |
| --- | --- | --- | --- | --- |
| Inner | 260.0 | 270.0 | 700.0 | 900.0 |
| Outer | 280.0 | 300.0 | 700.0 | 900.0 |

The residual magnetic field along the axis of a single 5 mm thick shell is about 4.5G, approximately ten times greater that the earth's magnetic field and larger than optimal for the linac 107. There are several options to further reduce this residual field. As shown in FIG. 4C, one option is to add a secondary shielding element 120 inside of the magnetic shield 118 to further reduce the magnetic field that is magnetically isolated from the first. For example, the secondary shielding element 120 can be a second shell 120 positioned inside of the first shell 118, where both shells are coaxial along the longitudinal axis p of the linac 107. In such embodiments, the second shell 120 can be of higher permeability, but of a lower saturation flux density of the outer shell 118, as the outer shell 118 has greatly reduced the magnetic field, e.g., mu-metal. It is preferable to magnetically isolate the shells 118 and 120 in order to gain the highest shielding by restarting the saturation of the metal.

Alternatively, the secondary shielding element 120 can be a current carrying coil that is located inside of the primary shell 118 to cancel the residual field. If the magnetic field remaining is sufficiently low and its value and direction in space are known, then it can be possible to make small adjustments in the accelerating portion of the linac The current linacs are configured to accommodate an electron beam that is at least substantially straight; if the beam were bent only a small amount by the field, the anticipated beam path can be calculated and the accelerating plates can be altered to accommodate the beam bending. Given the azimuthally symmetric nature of the fringe field, the path deviation of the electron beam should be largely independent of gantry position. As another alternative, the secondary shielding element 120 can be an RF shield 120, as further described below.

The peak-to-peak field in-homogeneity of the system main magnets 112a and 112b plus the double shell is 623.8 ppm over 45 cm DSV. This inhomogeneity is too large for MRI system 102, so additional shimming is desirable. The field inhomogeneity is mostly represented by a few of the tesseral harmonics; $S_{1,1} \rightarrow Y$, $C_{2,2} \rightarrow (X2-Y2)$, and $S_{3,1} \rightarrow Z2X$, and $S_{3,3} \rightarrow X3$. All of the major harmonics of significance are listed in Table 2.

TABLE 2

Spherical Harmonics over 45 cm DSV

| Zonal Harmonics [ppm] | | Tesseral harmonics [ppm] | | |
|---|---|---|---|---|
| n | $C_n$ | n | m | $C_{n,m}$ | $S_{n,m}$ |
| 1 | 1.625035E−03 | 1 | 1 | 6.6950990E−03 | −2.6417408E+02 |
| 2 | −9.190121E+01 | 2 | 1 | −4.3762731E−03 | −2.2226838E−03 |
| 3 | 4.274773E−03 | 2 | 2 | −2.3791910E+01 | −1.1871930E−03 |
| 4 | 8.878808E+00 | 3 | 1 | −1.1657569E−04 | 1.5830479E+01 |
| 5 | −2.132553E−03 | 3 | 2 | −1.9884826E−04 | 5.8882723E−04 |
| 6 | −6.259163E−01 | 3 | 3 | −1.0577878E−04 | 1.2089904E+00 |
| 7 | −7.645843E−03 | 4 | 1 | 3.2428894E−04 | −2.8578203E−05 |
| 8 | 3.513474E−01 | 4 | 2 | 8.1373300E−01 | 3.6183409E−05 |
| 9 | −9.504502E−03 | 4 | 3 | 7.2001599E−05 | 3.3853550E−05 |
| 10 | 2.238179E+00 | 4 | 4 | 4.2607165E−02 | −5.3185952E−06 |
| 11 | 6.139678E−03 | 5 | 1 | −2.7178914E−04 | −9.0437945E−01 |

The zonal harmonics can all be handled by shimming, and the shim setting does not change with rotation of the linac 107 around the Z-axis. Hence, the shims can be located on the MRI bore. The negative of the zonal harmonics could even be built into the magnets 112a and 112b so that the combination of magnets 112a, 112b plus magnetic shield 118 eliminates these terms. The tesseral harmonics are a larger problem because they would move with the linac orientation. The tesseral harmonics could be shimmed out with passive shims near the central plane CP on the gantry 106 that would move with the gantry 106/linac 107 rotation and/or with resistive shims built into the gradient coil that could be electrically adjusted to match the rotation of the gantry 106.

According to some embodiments, the system 100 as shown in FIGS. 1A-1D includes a linac 107 having a vertical acceleration axis and is mounted on the gantry 106 so that the linac 107 can be rotated about the radiotherapy and MRI 102 isocenters. The linac 107 is also preferred to be of low energy, in the range of 4 to 6 MV, and have a standing wave guide to keep it compact. The linac 107 can be configured to only produce photon beams that can be used for intensity modulated radiation therapy or conformal radiation therapy. The linac 107 can operate at either S-band or X-Band frequencies, but S-band is preferred for high output and stability. Referring to FIG. 4C, in this embodiment the element 120 can be configured to serve as an RF shield 120. In order to provide RF shielding, the RF shield shell 120 can be made of a suitable shielding material, for example copper foil, aluminum foil, or carbon fiber. Metals such as copper and aluminum tend to reflect RF radiation due to eddy currents on their surfaces. The carbon fiber materials tend to absorb RF energy.

In some embodiments, particularly where the RF shield shell is formed of conductive material, the eddy currents can be reduced by providing one or more slots that extend through the shield shell. For example, shield shell 120 is shown as having slots 120A and 120B in FIG. 4C. However, the size, number, and configuration of the slots can vary from that shown in FIG. 4C. Also, while shield shell 120 is shown with slots, such slots can also, or alternatively, be provided in shield shell 118; also, any number of such slots can be provided in any one or more of the shield shells in embodiments having more than one shield shell. Such slots can also be desirable in the magnetic shielding shells, and can thus be included in some embodiments of the magnetic shielding shells.

While FIG. 4C shows two layers (shield shells 120 and 118), alternative embodiments can include any number of layers. In some embodiments, the layers of shield shells can be made of combinations of different materials or of the same material. For example, in some embodiments, the shield shell layers can include alternating layers formed of RF absorbing material and RF reflecting material. In such embodiments, it is desirable to provide an air gap between the layers of shield shells.

Cooling can be provided by cooling system 115 (FIG. 1E) as needed to the absorbing material in the RF shield 120. A variety of known cooling methods can be used for cooling the RF shield 120. The cooling system 115 can include, for example, fluid-carrying conduit for circulating a fluid in the vicinity of one or more of the shield shells that form the RF shield 120. Also, air-cooling can be provided by incorporating a system for moving air across one or more surfaces of the shield shells that form the RF shield 120.

The magnetic shield 118 and the RF shield 120 are placed around the linac 107 to shield the path of the electrons from the electron gun 107b of the linac 107 to the target to a magnetic field strength on the order of the size of the earth's magnetic field strength. The magnetic shield 118 is arranged such that it is not in the path of the radiotherapy beam, for example as shown in FIGS. 4A and 4C. The RF shield 120 is also placed around the linac 107, rather than the MRI 102, and comprised of both absorptive and reflective layers to dissipate and absorb the RF radiation generated by the linac 107 before it can compromise the MRI function and they can function as part of the flattening filter. In some embodiments, the RF shield 120 can work in concert with a standard bore-mounted MRI RF shield. The beam from the linac 107 is allowed to pass through the RF shield 120 (as well as the bore mounted MRI RF shield in such embodiments) as long as the RF shield(s) are uniformly and minimally attenuating to the radiotherapy beam. It should be noted that in some embodiments, the RF shield 120 can be provided without the magnetic shield 118 where only the RF shielding may be desired.

Figure 4D:
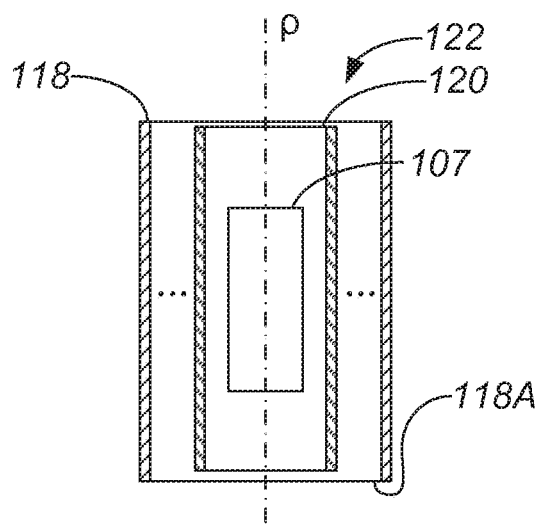
Figure 4E:
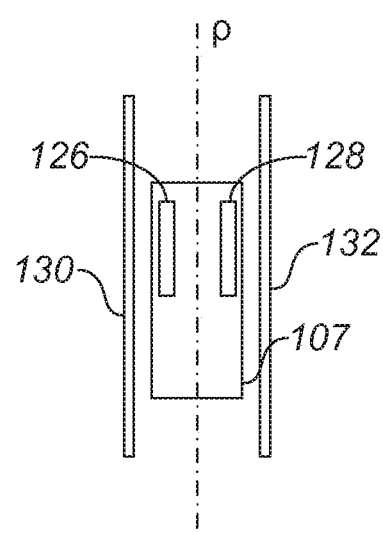

As mentioned above, in some embodiments, the secondary shielding element 120 shown in FIG. 4C can be a second magnetic shield 120. Referring to FIG. 4D, to suppress even further the magnetic B-field in the region where the linac 107 is located, a magnetic shield device 122 can include one or more concentric magnetic shields, which can include magnetic shields 118 and 120 as well as one or more additional magnetic shields. The magnetic shield device 122 can include the multiple magnetic shields, including shields 118 and 120, that are made of high magnetic susceptibility (and permeability) material. The shields of the magnetic shield device 122 can be concentrically placed inside of each other around the linac 107 accelerating structure. The magnetic shields of the magnetic shield device 122 can be magnetically and electrically isolated from each other with a suitable dielectric material such as air or plastic. Having multiple magnetic shields is beneficial because the magnetic field shielding of the material begins to saturate with depth. Introducing a new magnetic shield restarts the saturation effect providing increased shielding. Also, some embodiments such as the one shown in FIG. 4E can include a linac 107 having a split radiotherapy magnets 126 and 128 and a magnetic shield made of two isolated shells 130 and 132. The thickness of the magnetic shields of the embodiments shown in FIGS. 4A-4E can be chosen to be, for example, 5 mm, and the material can be selected to be 530-50AP steel material. Other material options for the magnetic shield 118 (as well as other magnetic shields disclosed herein) include M19 steel, M45 steel, and steel sold by ThyssenKrupp Steel under the trade name 530-50 AP. The outer diameter OD and length L of the shielding shells can be, for example, 27 cm and 30 cm, respectively, in a two-shell embodiment such as the one shown in FIG. 4C. The shells 118 and 120 can both be located at a fixed distance from the isocenter IC (in the present embodiment, about 85 cm) that is at or near the Bz field reversal location, although this is not a requirement. The location and size of the magnetic shields, including shields 118, 120, 130, 132, and any additional magnetic shields of the magnetic shield device 122, should be large enough to contain the linac 107, but not so long or narrow that it limits the size of the beam from the linac 107.

Figure 6A:
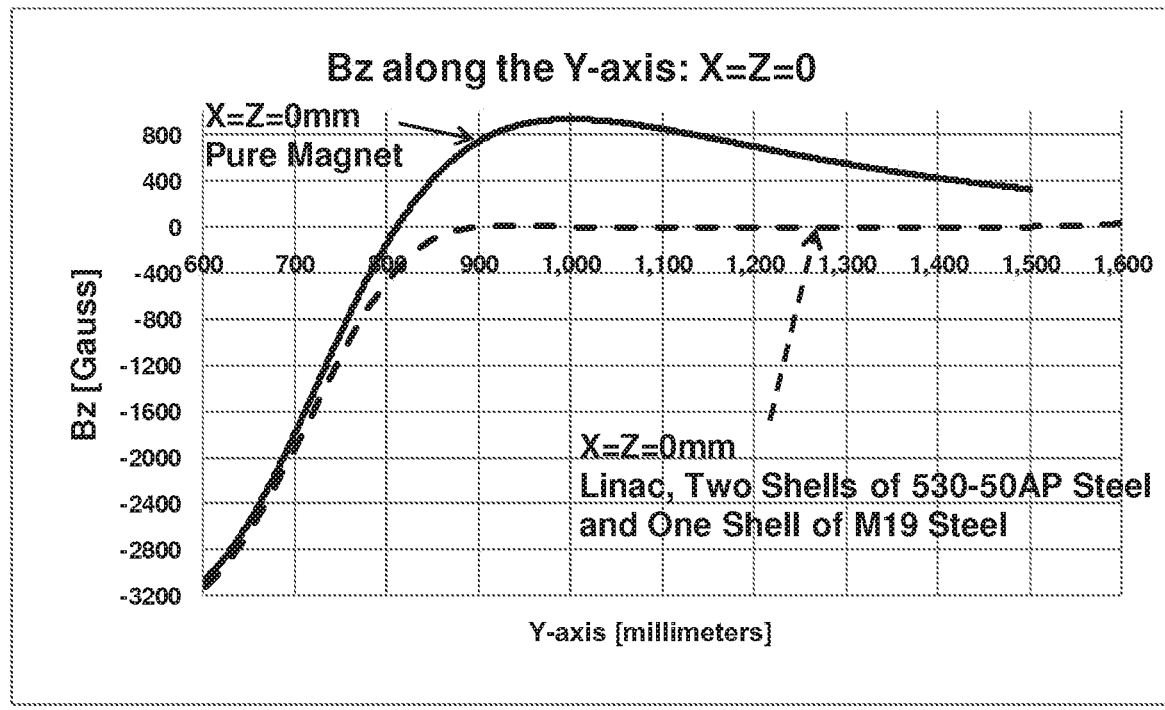
FIGS. 6A and 6B show a comparison of the shielded and unshielded Bz-field generated by the main magnets of the MRI according to the preferred embodiment.
Figure 6B:
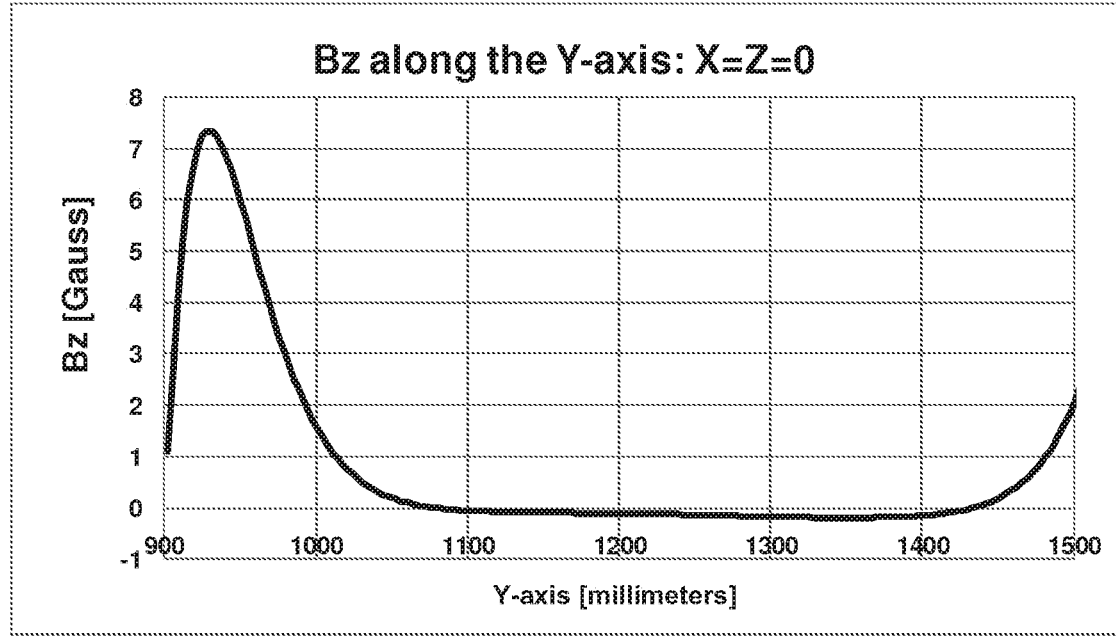

FIG. 6A shows a comparison of the Bz-field generated by the main magnets 112a and 112b, and the z-component of the Bz-field generated by the magnets 112a and 112b as shielded using a magnetic shield device 122 that includes three concentric shield shells. FIG. 6B shows a close-up view of the region of interest near Y=1000 mm of the z-component of the Bz-field generated by the main magnets 112a and 112b as shielded by the magnetic shield device 122. Table 3 lists the materials and dimensions of the magnetic shield device 122 according to the embodiments associated with FIGS. 6A and 6B. In the embodiment associated with FIGS. 6A and 6B and Table 3, the magnetic shield device 122 includes three concentric shells separated from each other by layers of air. As with other shielding shells disclosed herein, the shells of the shield device are preferably cylindrical, but can be other shapes. In Table 3, "ID" is the inner diameter, "OD" is the outer diameter, Length is the shell length L, and the "Starting Y-position" is the distance from the isocenter (Z-axis) to the respective bottom edges of the layers of the shield device 122.

TABLE 3

Steel M19 and Two Shells of 530-50AP Steel

| Layer | Material | ID [mm] | OD [mm] | Length [mm] | Starting Y-position [mm] |
|---|---|---|---|---|---|
| Inner | "M19" Steel | 244.0 | 254.0 | 700.0 | 900.0 |
| Middle | "530-50AP" Steel | 260.0 | 270.0 | 700.0 | 900.0 |
| Outer | "530-50AP" Steel | 280.0 | 300.0 | 700.0 | 900.0 |

The residual B-field is less than 1 Gauss in the region 1100 mm<y<1400 mm. This is roughly comparable to the earth's field close to the axis p. The harmonics of the magnetic field are close to the single shell model associated with the embodiment shown in FIG. 4B. The Peak-to-Peak field in-homogeneity over 45 cm DSV generated by the main magnets 112a and 112b plus the magnetic shields 118 and 120 is 623.6 ppm. It is preferable to have the best shielding on the electron gun 107b of the linac 107 and less shielding can be applied to the target end of the accelerating structure. This field in-homogeneity is mostly represented by the y-harmonic. The spherical harmonics are listed in Table 4.

TABLE 4

Two shells solution: Spherical Harmonics over 45 cm DSV

| Zonal Harmonics [ppm] | | Tesseral harmonics [ppm] | | | |
|---|---|---|---|---|---|
| n | $C_n$ | n | m | $C_{n,m}$ | $S_{n,m}$ |
| 1 | 1.6250352E−03 | 1 | 1 | 6.6950990E−03 | −2.6417408E+02 |
| 2 | −9.1901212E+01 | 2 | 1 | −4.3762731E−03 | −2.2226838E−03 |
| 3 | 4.2747730E−03 | 2 | 2 | −2.3791910E+01 | −1.1871930E−03 |
| 4 | 8.8788081E+00 | 3 | 1 | −1.1657569E−04 | 1.5830479E+01 |
| 5 | −2.1325528E−03 | 3 | 2 | −1.9884826E−04 | 5.8882723E−04 |
| 6 | −6.2591632E−01 | 3 | 3 | −1.0577878E−04 | 1.2089904E+00 |
| 7 | −7.6458435E−03 | 4 | 1 | 3.2428894E−04 | −2.8578203E−05 |
| 8 | 3.5134737E−01 | 4 | 2 | 8.1373300E−01 | 3.6183409E−05 |
| 9 | −9.5045015E−03 | 4 | 3 | 7.2001599E−05 | 3.3853550E−05 |
| 10 | 2.2381795E+00 | 4 | 4 | 4.2607165E−02 | −5.3185952E−06 |
| 11 | 6.1396783E−0 | 5 | 1 | −2.7178914E−04 | −9.0437945E−01 |

Figure 7A:
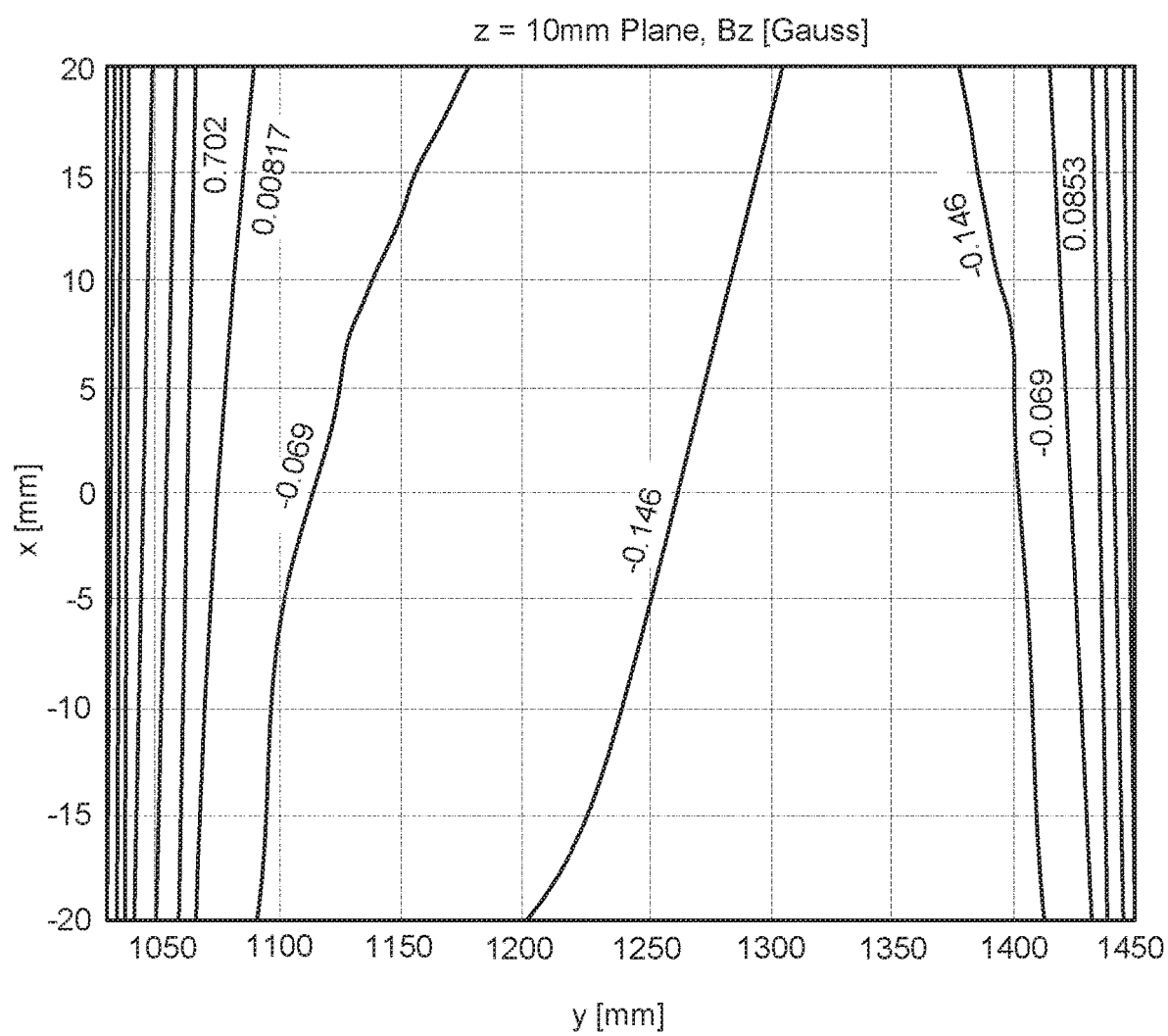
FIGS. 7A and 7B show the Bz-field map inside the preferred embodiment of a magnetic shield in the XY planes at Z=10 mm and Z=20 mm respectively.
Figure 7B:
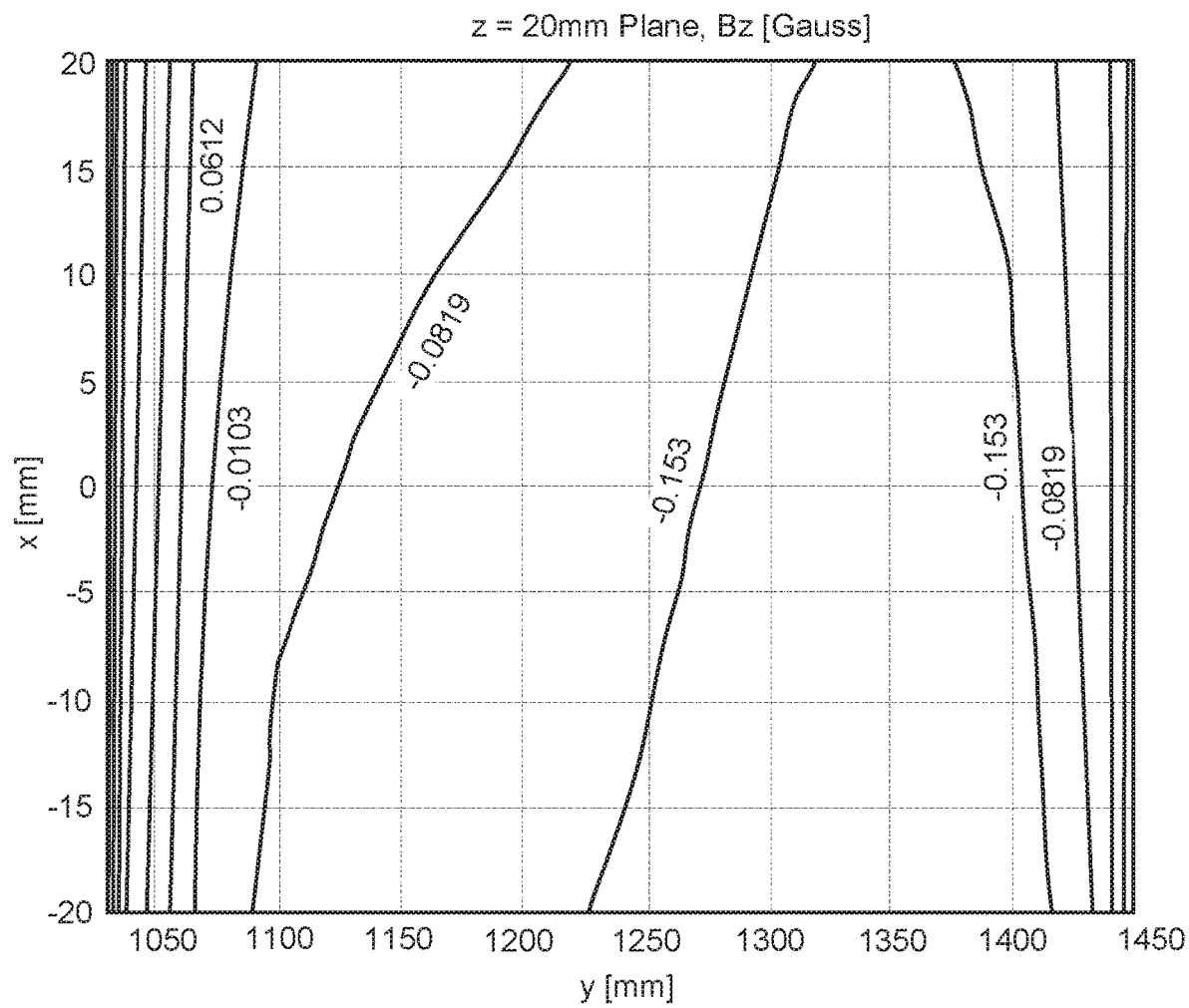

The methods to be used to shim out this inhomogeneity are the same as those proposed in the case of the single shell model. FIGS. 7A and 7B show the Bz-field map inside the inner shell in the XY planes at Z=10 mm and Z=20 mm, respectively.

Figure 8:
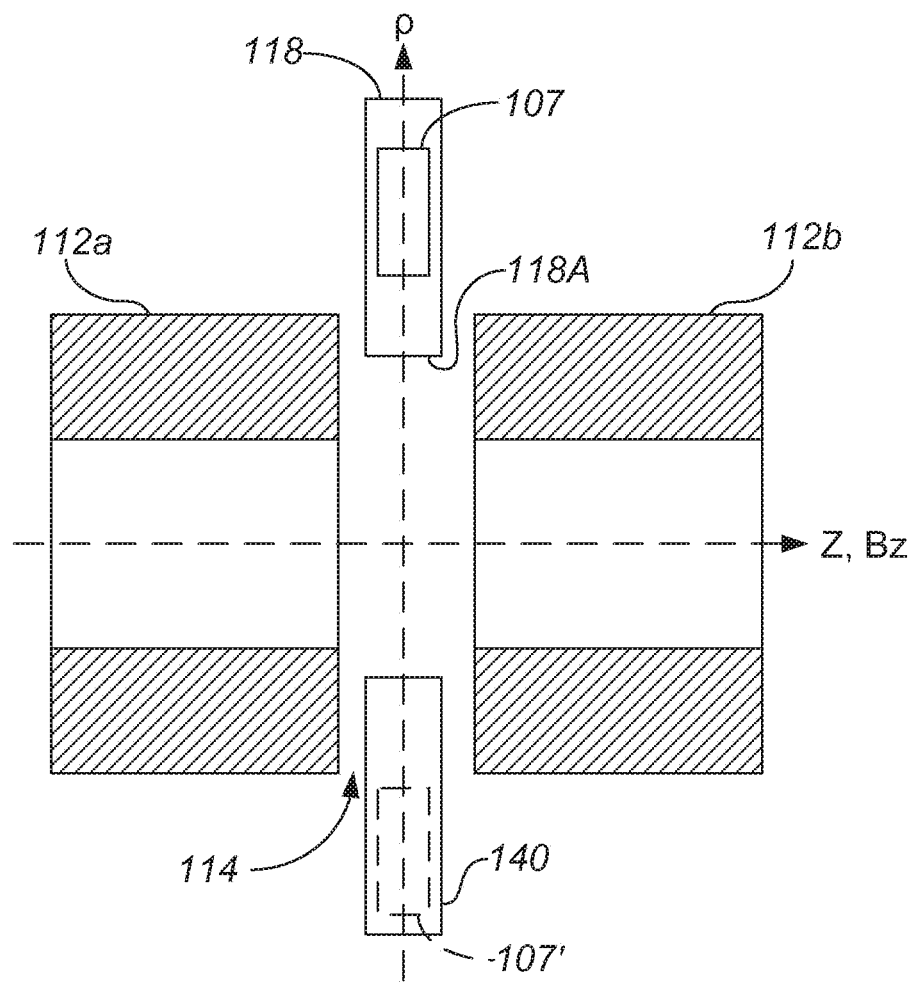
FIG. 8 shows a simplified block diagram of some embodiments of the system shown in FIGS. 1A-1D, including a section view of the main magnets shown in FIGS. 1C and 1D.

Referring next to FIG. 8, another embodiment will be described that can reduce field in-homogeneity caused by the presence of a linac shield, such as the shield 118 shown in FIGS. 4A and 4B. The embodiment shown in FIG. 8 can be similar to the embodiment shown in FIGS. 4A and 4B, and like components have retained the same element numbers; description of those components applies equally here, so the description is not repeated. In the embodiment shown in FIG. 8, the first shield 118 extends along a first longitudinal axis $\rho_1$ and a second shield 140 (which can optionally include a second linac 107') extends along a second longitudinal axis $\rho_2$ symmetrically 180° apart from the first longitudinal axis $\rho_1$ of the first magnetic shield 118. Each of the axes $\rho_1$ and $\rho_2$ is on the central plane CP. In some embodiments, the second shield 140 can be formed of a magnetically shielding material, such as steel sold by ThyssenKrupp Steel under the trade name 530-50 AP, as described in connection with magnetic shield 118. Other material options for the magnetic shield 118 (as well as other magnetic shields disclosed herein) include M19 steel, M45 steel, and Carpenter 49 steel. If only a second symmetric shield 140 is present, this solution can be thought of as a symmetric shim for the primary shell 118. In some embodiments, one or both of the magnetic shields 118 and 140 can be magnetic shield devices that include two or more concentric magnetic shield shells, such as shown in FIG. 4C or FIG. 4D.

FIG. 9 shows the Bz-field generated by the main magnets 112a and 112b and in an embodiment where both the magnetic shield 118 and the magnetic shield 140 include two concentric magnetic shielding shells. In this embodiment, the peak-to-peak field in-homogeneity over 45 cm DSV generated by the system main magnets 112a and 112b plus the two double-shell shield (118+140) is 416.96 ppm. This field in-homogeneity is mostly generated by the Z2 harmonic. The Y-harmonics all become negligible small because of the Y symmetry. The harmonics for this case are listed in Table 4.

TABLE 4

Two double shells solution: Spherical Harmonics over 45 cm DSV

| Zonal Harmonics [ppm] | | Tesseral harmonics [ppm] | | |
|---|---|---|---|---|
| n | $C_n$ | n m | $C_{n,m}$ | $S_{n,m}$ |
| 1 | −1.1158532E−03 | 1  1 | −1.3130497E−04 | −1.3130497E−04 |
| 2 | −1.7798728E+02 | 2  1 | 9.4937074E−05 | 9.4937074E−05 |
| 3 | 7.9200018E−03 | 2  2 | −4.7129252E+01 | −9.2290614E−03 |
| 4 | 1.7600141E+01 | 3  1 | 4.5203733E−06 | 4.5203734E−06 |
| 5 | −2.2793685E−03 | 3  2 | −4.0735120E−05 | −8.2531950E−04 |
| 6 | −1.3166284E+00 | 3  3 | 1.0363288E−05 | −1.0363288E−05 |
| 7 | −1.3414318E−02 | 4  1 | −7.1884515E−05 | −7.1884515E−05 |
| 8 | 4.0916507E−01 | 4  2 | 1.6230890E+00 | 2.4395720E−04 |
| 9 | −1.8969599E−02 | 4  3 | −5.7802678E−06 | 5.7802678E−06 |
| 10 | 2.2510390E+00 | 4  4 | 8.3827275E−02 | 1.3021016E−05 |
| 11 | 1.0428939E−02 | 5  1 | 5.3620187E−05 | 5.3620187E−05 |

The zonal harmonics are now twice as large as in the single shell model associated with the embodiment shown in FIG. 4B. However, they can all be handled by passive shimming, and the shim setting does not change with rotation of the linac 107 around the Z-axis. The negative of the zonal harmonics could even be built into the main magnets 112a and 112b so that the combination of main magnets 112a and 112b plus shield shells 118 and 140 eliminates these terms. The Tesseral harmonics are a larger problem because they would move with the linac 107 rotational position. However, symmetry eliminates the worst of the harmonics. The Tesseral harmonics can be shimmed out with passive shims near the central plane on the linac gantry 106 and/or with resistive electrical shims. Passive shims built into the rotating gantry 106 can be permanent magnet shims at these magnetic field levels (oriented magnetization shims for more shim options). Passive shims can be added at a smaller radius to reduce the material required in the shims. Resistive electrical shims in the gradient would change with the rotation of the linac gantry.

In still further embodiments, there can be N sets of magnetic shield shells identical or similar to magnetic shield 118, each having a respective axis $\rho_1$ through $\rho_N$. Such embodiments can be arranged in a manner similar to the embodiment shown in FIG. 8. Each of the axes $\rho_1$ through $\rho_N$ is on the central plane CP and angularly separated by an angle=360°/N. The higher the N, the more that the net effect of the Tesseral harmonics can be canceled out. Also, since the magnetic shield shells tend to act as RF shields, multiple shells are advantageous for providing RF shielding.

In some embodiments, as shown in FIG. 10, there can be two parallel annulus discs 144 and 146 made of high relative permeability material. They can be a part of the gantry 106 and on opposing sides of the linac 107. In this case, the Tesseral spherical harmonics should be relatively small, and the Zonal harmonics should be relatively big. Placing two annulus discs 144 and 146 in some sense are equivalent to two extra coils in the main magnet 112a, 112b. Optimally, the main magnet 112a, 112b can be designed to accommodate two annulus discs 144 and 146.

The magnetic field from the main magnets 112a and 112b at 1 meter from isocenter along the Y-axis is difficult to shield without the field reduction of passive shields, such as shield 118 described above. However, after the magnetic shielding provided by the ferromagnetic material, the residual field is near 5-7 Gauss. This residual field can easily be shimmed out with DC current in a coil, for example in embodiments where the secondary shielding element 120 shown in FIG. 4C is a coil 120'. A schematic view of the shielding coil 120' is shown in FIG. 11. The coil 120' can be cylindrical, having a half-length L and radius R and designed according to the following method (although shapes other than cylindrical can be used). The shielding coil 120' should preferably produce the magnetic flux field Bx (in local system of coordinates) that cancels the Bz component of the magnetic field (in the original system of coordinates) generated by the main magnets 112a and 112b.

The current density on the cylinder of radius R can be presented in the following form:

$$\vec{J}(\rho,\varphi,z) = \delta(\rho-R)\{\vec{e}_\varphi f_\varphi(z)\cos(\varphi) + \vec{e}_z f_Z(z)\sin(\varphi)\}$$

$$\nabla \vec{J} = 0 \Rightarrow f_\varphi(z) = f_Z'(z)$$

The magnetic potentials generated by this current can be expressed as follows:

$$A_\rho(\rho,\varphi,z) = \frac{\mu R^2}{2\pi}\sin(\varphi)\int_0^\infty k\,dk(T_2(k,\rho,R) - T_0(k,\rho,R))F_S(k,z)$$

$$A_\varphi(\rho,\varphi,z) = -\frac{\mu R^2}{2\pi}\cos(\varphi)\int_0^\infty k\,dk(T_2(k,\rho,R) + T_0(k,\rho,R))F_S(k,z)$$

$$A_Z(\rho,\varphi,z) = \frac{\mu R}{\pi}\sin(\varphi)\int_0^\infty dk\,T_1(k,\rho,R)F_C(k,z)$$

$$F_C(k,z) = \int_{L_1}^{L_2} f_Z(z')\cos(k(z-z'))dz'$$

$$F_S(k,z) = \int_{L_1}^{L_2} f_Z(z')\sin(k(z-z'))dz'$$

$$T_n(k,\rho,R) = \theta(\rho-R)I_n(kR)K_n(k\rho) + \theta(R-\rho)K_n(kR)I_n(k\rho), n = 0, 1, 2$$

In this equation, $I_n(k\rho), K_n(k\rho)$ are modified Bessel functions. The transverse components of the magnetic field can be presented in the following form:

$$B_\rho(\rho,\varphi,z) = -\frac{\mu R^2}{\pi}\cos(\varphi)\int_0^\infty k^2\,dk(\theta(\rho-R)I_n'(kR)K_n'(k\rho) +$$

-continued $$B_\varphi(\rho, \varphi, z) = \frac{\mu R^2}{\pi \rho} \sin(\varphi) \int_0^\infty k^2 dk (\theta(\rho - R) I'_n(kR) K_n(k\rho) + \theta(R-\rho) K'_n(kR) I'_n(k\rho)) F_C(k, z)$$
$$\theta(R-\rho) K'_n(kR) I_n(k\rho)) F_C(k, z)$$

$n = 0, 1, 2$

The Bx-component of the magnetic flux field inside the cylinder of the coil 120' is:

$$B_X(\rho, \varphi, z) = -\frac{\mu R^2}{2\pi} \int_0^\infty k^2 dk I_0(k\rho) K'_1(kR) F_C(k, z) - \frac{\mu R^2}{2\pi} \cos(2\varphi) \int_0^\infty k^2 dk I_2(k\rho) K'_1(kR) F_C(k, z)$$

This Bx-component (in the local system of coordinates) should cancel the Bz'-component produced by the magnet. This suggests that a minimization procedure can be applied (similar to that of the gradient design) to find the currents density $f_Z(z)$. We consider a functional to be minimized:

$$W = E + \frac{\Lambda}{2\mu} \sum_{i \in V_{Linac}} [B_X^{Coil}(r_i) - B_{Z,i}^{Magnet}]^2 + \frac{\beta}{2\mu} \sum_{i \in DSV} [B_X^{Coil}(r_i)]^2 + \frac{\mu \lambda}{2} \left\| \frac{\partial^k f_Z(z)}{\partial z^k} \right\|_2^2$$

In the above equation, E is the energy of the coil 120', the second term is to minimize the deviation of the field produced by the shielding coil 120' from that of the main magnets 112a, 112b, the third term is to minimize the effect of the shield coil 120' on the field in-homogeneity in the imaging volume, and the last term is introduced as to limit the current density. The coefficients Λ, β, and λ are the weighting factors; λ can be a regularization parameter to minimize the current in the shielding coil 120'.

The current density $f_Z(z)$ can be expressed in terms of a basis functions. It should be mentioned that the current density $f_Z(z)$ is zero at the ends of the shielding coil 120'.

$$f_Z(z) = \sum_{n=1} a_n \Phi_n^C(z, L) + \sum_{n=1} b_n \Phi_n^S(z, L)$$

$$\Phi_n^C(z, L) = \cos(k_n^C z), \Phi_n^S(z, L) = \sin(k_n^S z)$$

$$k_n^C = \frac{\pi(2n-1)}{2L}, k_n^S = \frac{\pi n}{L}$$

The coefficients $\alpha_n$ can be found from the following equation:

$$\frac{\partial W}{\partial a_n} = 0, \frac{\partial W}{\partial b_n} = 0$$

This is leading to a system of linear equation for the coefficients $\alpha_n$. The energy E has the following form:

$$E = -\frac{\mu R^2}{2} \int_0^\infty dk (kR)^2 I'_1(kR) K'_1(kR) < f_Z \cos(k()) f_Z > = \frac{\mu}{2} \sum_{n,m=1} A_n W_{n,m} A_m$$

$$A_\alpha = \begin{pmatrix} a_n \\ b_m \end{pmatrix}$$

$$W_{\alpha,\beta} = -R^2 \int_0^\infty dk (kR)^2 I'_1(kR) K'_1(kR) < \Phi_\alpha \cos(k()) \Phi_\beta > \Phi_\alpha = \begin{pmatrix} \Phi_n^S \\ \Phi_n^C \end{pmatrix}$$

$$<\Phi_\alpha \cos(k()) \Phi_\beta> = \int_L^{L_2} \int_L^{L_2} \Phi_\alpha(z) \cos(k(z-z')) \Phi_\beta(z') dz dz'$$

The field produced by the shield coil 120' has the following form:

$$B_X^{Coil}(r) = \mu \sum_\alpha A_\alpha B_{X,\alpha}^{Coil}(r)$$

$$B_{X,\alpha}^{Coil}(r) = -\frac{R^2}{2\pi} \int_0^\infty dk I_0(k\rho) K'_1(kR) \Psi_{C,\alpha}(k, z) - \frac{R^2}{2\pi} \cos(2\varphi) \int_0^\infty k^2 dk I_2(k\rho) K'_1(kR) \Psi_{C,\alpha}(k, z)$$

$$\Psi_{C,\alpha}(k, z) = \int_{L_1}^{L_2} \Phi_\alpha(z') \cos(k(z-z')) dz'$$

$$\left\| \frac{\partial^k f_Z(z)}{\partial z^k} \right\|_2^2 = L \sum_{n=1} a_n^2 (k_n^C)^{2k} + b_n^2 (k_n^S)^{2k}$$

Then the equation for the unknown A holds:

$$\sum_\beta Z_{\alpha,\beta} A_\beta = K_\alpha$$

$$Z_{\alpha,\beta} = W_{\alpha,\beta} + \alpha \sum_{i \in V} B_{X,\alpha}^{Coil}(r_i) B_{X,\beta}^{Coil}(r_i) + \beta \sum_{i \in DSV} B_{X,n}^{Coil}(r_i) B_{X,m}^{Coil}(r_i) + \lambda \delta_{\alpha,\beta} \frac{k_n^{2k}}{2} L$$

$$K_\alpha = \frac{\Lambda}{\mu} \sum_{i \in V} B_{X,\alpha}^{Coil}(r_i) B_Z^{Magnet}(r_i)$$

The matrix $Z_{\alpha\beta}$ is positive defined and does not have zero eigenvalue, thus:

$$a_\alpha = \sum_\beta (Z^{-1})_{\alpha,\beta} K_\beta$$

This defines the solution for the current density.

Figure 12A:
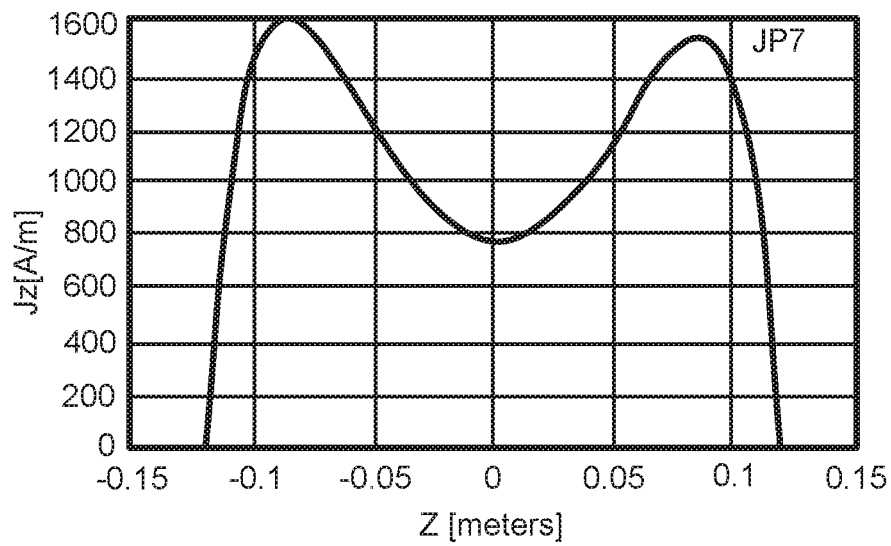
FIGS. 12A-12B show the z-component of the magnetic field generated by the main MRI magnets before and after, respectively, activation of the active coil shown in FIG. 11.
Figure 12B:
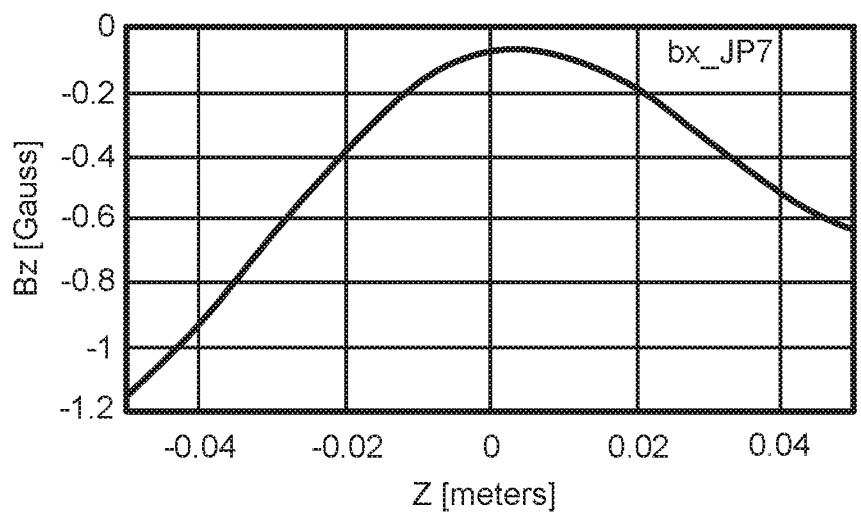

Some embodiments can include a combined passive shield and active coil. The residual Bz-field shown in FIG. 5b (a single shell case) was used as an input data. The radius of the coil 120' was chosen to be 75 mm and the half length L was chosen to be L=180 mm. The center of the coil 120' is located at y=1051 mm. FIG. 12A shows the z-component of the current density on the active shield coil 120' prior to activation (i.e., prior to application of an electric current) of the coil 120', and FIG. 12B shows the residual Bz-field after activation of the shield coil 120'.

The following parameters Λ, β, K, and λ, were used: Λ=1, β=0, K=1, and λ=0.0001. The parameter β that accounts for the effect of correcting the in-homogeneity inside the DSV was chosen to be zero because the level of the residual field of FIG. 5B is already small (of the order of 7 Gauss) and the active shield coil is located far from the imaging volume.

Some embodiments can include a completely active coil shielding system. In such embodiments, the shielding of the linac 107 can be accomplished locally using only the above-described active current-carrying coils, such as coil 120', in place of the passive magnetic shields in embodiments described above. The coils 120' can be arranged to simply cancel the field at the linac 107 and can also incorporate an active shield to reduce the influence on the homogeneity of the main magnetic field.

Still another alternative way of shielding the linac 107 locally is to use a distribution of permanent magnets. They can be arranged to simply cancel the field at the linac 107 and can also incorporate an active shield, such as coil 120', to reduce the influence on the homogeneity of the main magnetic field from the main magnets 112a and 112b.

All possible combinations of the disclosed embodiments are also possible. Small variations to the shields and distributions of the shielding materials, current carrying coils, and magnet distributions are also possible.

It should be noted that the magnetic shields described herein, such as shields 118, 120, 122, 130, 132, and others experience a force from the main magnets 112a and 112b of the MRI 102. Thus, the mounting for the shields is preferably designed to withstand such magnetic forces.

The high-power RF source and waveguide for the linac 107 can also be enclosed, or partially enclosed, within the magnetic shields disclosed herein. The RF shielding can be extended to contain some or all components of the linac 107.

Regarding RF screening for the MRI 102, clinical linacs suitable for use as linac 107 can operate in the S-band frequency range accelerate electrons to about 6 MeV using RF microwave cavities at ~3 GHz. While this frequency is well above the 15 MHz of the MRI system 102, it involves megawatts of RF power pulse with a frequency of several hundred Hertz. Sidebands in the RF power source can excite/reflect from other materials causing interference with the operation of the MRI system 102. As mentioned above in connection with FIG. 4B, the element 120 can be an RF shield that is placed around the linac 107 made of RF absorbing, RF reflecting, or a combination of both can effectively eliminate the RF interference with the MRI system 102. Additionally, the MRI RF room, which can be made of RF reflecting material that can bound RF from the linac 107 into the MRI 102, can be lined on the interior surface with a wall covering of RF absorbing material, e.g., meshed or chopped carbon fiber, carbon fiber wallpaper, carbon fiber panels, or carbon fiber paint, and eliminate RF reaching the MRI. The gantry 106 and area around the RF source of the linac 107 can be covered in RF absorbers, reflectors, and combinations of both to reduce the ambient (environmental) RF fields. At 3 GHz (microwave ovens are at 2.45 GHz) the RF will produce dielectric heating of polarized molecules such as water. Thus, a variety of polarized molecule materials can be used as RF absorber for the RF energy. In a split magnet system, some of the conductive surfaces that divert RF energy in a closed system are missing in the magnet gap 114. An RF shield about the MRI bore can be used in conjunction with the other shielding method described above. The RF shields do not add significantly to the beam attenuation so that the quality of the radiotherapy is significantly compromised. The conductive shielding may or may not be grounded to the magnet. If these surfaces were made of aluminum, such as aluminum foil, the beam attenuation would even be less than using copper. If the gradient coil is wound on a former one can construct the former out of carbon fiber for isolation from the linac system.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A system comprising:
   one or more magnets positioned along a longitudinal axis and configured to generate a magnetic field, at least a portion of the magnetic field extending along the longitudinal axis;
   a gantry rotatable about the longitudinal axis independently of the one or more magnets; and
   a plurality of shims mounted to the gantry that at least partially correct an inhomogeneity of the magnetic field that arises due to a rotational movement of the gantry.

2. The system of claim 1, wherein at least a portion of the plurality of shims are passive shims.

3. The system of claim 1, wherein at least a portion of the plurality of shims are permanent magnet shims.

4. The system of claim 1, wherein at least a portion of the plurality of shims are located near a central plane on the gantry.

5. The system of claim 1, wherein the plurality of shims are mounted to the gantry at a smaller radius to reduce the material required.

6. The system of claim 1, wherein the plurality of shims are configured to correct tesseral harmonics.

7. The system of claim 1, further comprising a linear accelerator mounted on the gantry whereby the plurality of shims mounted to the gantry are able to rotate with the linear accelerator.

* * * * *